(12) United States Patent
Conklin et al.

(10) Patent No.: US 7,151,166 B2
(45) Date of Patent: *Dec. 19, 2006

(54) ANTIBODY TO MAMMALIAN CYTOKINE-LIKE POLYPEPTIDE-10

(75) Inventors: Darrell C. Conklin, Seattle, WA (US); Betty A. Haldeman, Seattle, WA (US)

(73) Assignee: ZymoGenetics, Inc., Seattle, WA (US)

( * ) Notice: Subject to any disclaimer, the term of this patent is extended or adjusted under 35 U.S.C. 154(b) by 470 days.

This patent is subject to a terminal disclaimer.

(21) Appl. No.: 10/789,968

(22) Filed: Feb. 27, 2004

(65) Prior Publication Data

US 2004/0152878 A1 Aug. 5, 2004

Related U.S. Application Data

(63) Continuation of application No. 10/413,661, filed on Apr. 15, 2003, now Pat. No. 7,115,714, which is a continuation of application No. 09/313,458, filed on May 17, 1999, now Pat. No. 6,576,743, which is a continuation-in-part of application No. 09/199,586, filed on Nov. 25, 1998, now abandoned.

(60) Provisional application No. 60/066,597, filed on Nov. 26, 1997.

(51) Int. Cl.
*C07K 16/24* (2006.01)
*C12N 5/12* (2006.01)

(52) U.S. Cl. ................ 530/388.23; 530/387.1; 530/387.2; 530/387.9; 530/388.1; 435/326; 436/547

(58) Field of Classification Search .............. None
See application file for complete search history.

(56) References Cited

U.S. PATENT DOCUMENTS 5,723,299 A 3/1998 Bell et al. ............... 435/7.1

OTHER PUBLICATIONS

Incyte Pharmaceuticals Inc., INC819592, Mar. 5, 1996.
Incyte Pharmaceuticals Inc., INC4304592, Jul. 9, 1998.
Wuyts et al., "Isolation of the CXC chemokines ENA-78, GROα and GROγ from tumor cells and leukocytes reveals $NH_2$-terminal heterogeneity. Functional comparison of different natural isoforms," *Eur J. Biochem* 260:421-429, 1999.
Rohovsky et al., "Growth factors and angiogenesis in wound healing," Growth Factors Would Healing, Eds: Ziegler T.R., Pierce G.F., Herndon D.N.; Pub: Springer New York N.Y., pp. 8-26, 1997.
Dlavin, "Cytokines and tissue repair," *J. Immunol. Immunopharmacol* 17(1):25-29, 1997.
George et al., "Macromolecular Sequencing & Synthesis," pp. 127-149, Ch. 12, Alan R. Liss, Inc., 1988.
Harlow et al., "Antibodies A Laboratory Manual," p. 76, Ch. 5, Cold Springs Harbor Laboratory, 1988.
Cunningham et al., *Science* 244:1081-1085, 1989.

*Primary Examiner*—Prema Mertz
(74) *Attorney, Agent, or Firm*—Shelby J. Walker

(57) ABSTRACT

A mammalian cytokine-like polypeptide, called Mammalian Cytokine-like polypeptide-10, (Zcyto10), polynucleotides encoding the same, antibodies which specifically bind to the polypeptide, and anti-idiotypic antibodies which bind to the antibodies. Zcyto10 is useful for promoting the healing of wounds and for stimulating the proliferation of platelets.

22 Claims, No Drawings

SEQUENCE LISTING

```
<160> NUMBER OF SEQ ID NOS: 43

<210> SEQ ID NO 1
<211> LENGTH: 926
<212> TYPE: DNA
<213> ORGANISM: Homo sapiens
<220> FEATURE:
<221> NAME/KEY: CDS
<222> LOCATION: (45)...(572)

<400> SEQUENCE: 1
ctttgaattc ctagctcctg tggtctccag atttcaggcc taag atg aaa gcc tct       56
                                              Met Lys Ala Ser
                                                1 agt ctt gcc ttc agc ctt ctc tct gct gcg ttt tat ctc cta tgg act      104
Ser Leu Ala Phe Ser Leu Leu Ser Ala Ala Phe Tyr Leu Leu Trp Thr
  5              10                 15                  20 cct tcc act gga ctg aag aca ctc aat ttg gga agc tgt gtg atc gcc      152
Pro Ser Thr Gly Leu Lys Thr Leu Asn Leu Gly Ser Cys Val Ile Ala
             25                  30                  35 aca aac ctt cag gaa ata cga aat gga ttt tct gac ata cgg ggc agt      200
Thr Asn Leu Gln Glu Ile Arg Asn Gly Phe Ser Asp Ile Arg Gly Ser
         40                  45                  50 gtg caa gcc aaa gat gga aac att gac atc aga atc tta agg agg act      248
Val Gln Ala Lys Asp Gly Asn Ile Asp Ile Arg Ile Leu Arg Arg Thr
     55                  60                  65 gag tct ttg caa gac aca aag cct gcg aat cga tgc tgc ctc ctg cgc      296
Glu Ser Leu Gln Asp Thr Lys Pro Ala Asn Arg Cys Cys Leu Leu Arg
 70                  75                  80 cat ttg cta aga ctc tat ctg gac agg gta ttt aaa aac tac cag acc      344
His Leu Leu Arg Leu Tyr Leu Asp Arg Val Phe Lys Asn Tyr Gln Thr
 85                  90                  95                 100 cct gac cat tat act ctc cgg aag atc agc agc ctc gcc aat tcc ttt      392
Pro Asp His Tyr Thr Leu Arg Lys Ile Ser Ser Leu Ala Asn Ser Phe
                105                 110                 115 ctt acc atc aag aag gac ctc cgg ctc tgt cat gcc cac atg aca tgc      440
Leu Thr Ile Lys Lys Asp Leu Arg Leu Cys His Ala His Met Thr Cys
            120                 125                 130 cat tgt ggg gag gaa gca atg aag aaa tac agc cag att ctg agt cac      488
His Cys Gly Glu Glu Ala Met Lys Lys Tyr Ser Gln Ile Leu Ser His
        135                 140                 145 ttt gaa aag ctg gaa cct cag gca gca gtt gtg aag gct ttg ggg gaa      536
Phe Glu Lys Leu Glu Pro Gln Ala Ala Val Val Lys Ala Leu Gly Glu
    150                 155                 160 cta gac att ctt ctg caa tgg atg gag gag aca gaa taggaggaaa           582
Leu Asp Ile Leu Leu Gln Trp Met Glu Glu Thr Glu
165                 170                 175 gtgatgctgc tgctaagaat attcgaggtc aagagctcca gtcttcaata cctgcagagg    642
aggcatgacc ccaaaccacc atctctttac tgtactagtc ttgtgctggt cacagtgtat    702
cttatttatg cattacttgc ttccttgcat gattgtcttt atgcatcccc aatcttaatt    762
```

-continued

```
gagaccatac ttgtataaga tttttgtaat atctttctgc tattggatat atttattagt      822
taatatattt atttattttt tgctattaat gtatttaatt ttttacttgg gcatgaaact      882
ttaaaaaaaa ttcacaagat tatatttata acctgactag agca                      926
```

```
<210> SEQ ID NO 2
<211> LENGTH: 176
<212> TYPE: PRT
<213> ORGANISM: Homo sapiens

<400> SEQUENCE: 2
```

```
Met Lys Ala Ser Ser Leu Ala Phe Ser Leu Leu Ser Ala Ala Phe Tyr
 1               5                   10                  15

Leu Leu Trp Thr Pro Ser Thr Gly Leu Lys Thr Leu Asn Leu Gly Ser
            20                  25                  30

Cys Val Ile Ala Thr Asn Leu Gln Glu Ile Arg Asn Gly Phe Ser Asp
        35                  40                  45

Ile Arg Gly Ser Val Gln Ala Lys Asp Gly Asn Ile Asp Ile Arg Ile
    50                  55                  60

Leu Arg Arg Thr Glu Ser Leu Gln Asp Thr Lys Pro Ala Asn Arg Cys
65                  70                  75                  80

Cys Leu Leu Arg His Leu Leu Arg Leu Tyr Leu Asp Arg Val Phe Lys
                85                  90                  95

Asn Tyr Gln Thr Pro Asp His Tyr Thr Leu Arg Lys Ile Ser Ser Leu
            100                 105                 110

Ala Asn Ser Phe Leu Thr Ile Lys Lys Asp Leu Arg Leu Cys His Ala
        115                 120                 125

His Met Thr Cys His Cys Gly Glu Glu Ala Met Lys Lys Tyr Ser Gln
    130                 135                 140

Ile Leu Ser His Phe Glu Lys Leu Glu Pro Gln Ala Ala Val Val Lys
145                 150                 155                 160

Ala Leu Gly Glu Leu Asp Ile Leu Leu Gln Trp Met Glu Glu Thr Glu
                165                 170                 175
```

```
<210> SEQ ID NO 3
<211> LENGTH: 793
<212> TYPE: DNA
<213> ORGANISM: Homo sapiens
<220> FEATURE:
<221> NAME/KEY: CDS
<222> LOCATION: (45)...(497)

<400> SEQUENCE: 3
```

```
ctttgaattc ctagctcctg tggtctccag atttcaggcc taag atg aaa gcc tct      56
                                             Met Lys Ala Ser
                                              1 agt ctt gcc ttc agc ctt ctc tct gct gcg ttt tat ctc cta tgg act     104
Ser Leu Ala Phe Ser Leu Leu Ser Ala Ala Phe Tyr Leu Leu Trp Thr
 5               10                  15                  20 cct tcc act gga ctg aag aca ctc aat ttg gga agc tgt gtg atc gcc     152
Pro Ser Thr Gly Leu Lys Thr Leu Asn Leu Gly Ser Cys Val Ile Ala
            25                  30                  35 aca aac ctt cag gaa ata cga aat gga ttt tct gac ata cgg ggc agt     200
Thr Asn Leu Gln Glu Ile Arg Asn Gly Phe Ser Asp Ile Arg Gly Ser
        40                  45                  50 gtg caa gcc aaa gat gga aac att gac atc aga atc tta agg agg act     248
Val Gln Ala Lys Asp Gly Asn Ile Asp Ile Arg Ile Leu Arg Arg Thr
    55                  60                  65 gag tct ttg caa gac aca aag cct gcg aat cga tgc tgc ctc ctg cgc     296
Glu Ser Leu Gln Asp Thr Lys Pro Ala Asn Arg Cys Cys Leu Leu Arg
```

-continued

```
Glu Ser Leu Gln Asp Thr Lys Pro Ala Asn Arg Cys Cys Leu Leu Arg
     70                  75                  80 cat ttg cta aga ctc tat ctg gac agg gta ttt aaa aac tac cag acc      344
His Leu Leu Arg Leu Tyr Leu Asp Arg Val Phe Lys Asn Tyr Gln Thr
 85                  90                  95                 100 cct gac cat tat act ctc cgg aag atc agc agc ctc gcc aat tcc ttt      392
Pro Asp His Tyr Thr Leu Arg Lys Ile Ser Ser Leu Ala Asn Ser Phe
                105                 110                 115 ctt acc atc aag aag gac ctc cgg ctc tgt ctg gaa cct cag gca gca      440
Leu Thr Ile Lys Lys Asp Leu Arg Leu Cys Leu Glu Pro Gln Ala Ala
            120                 125                 130 gtt gtg aag gct ttg ggg gaa cta gac att ctt ctg caa tgg atg gag      488
Val Val Lys Ala Leu Gly Glu Leu Asp Ile Leu Leu Gln Trp Met Glu
        135                 140                 145 gag aca gaa taggaggaaa gtgatgctgc tgctaagaat attcgaggtc              537
Glu Thr Glu
        150 aagagctcca gtcttcaata cctgcagagg aggcatgacc ccaaaccacc atctctttac    597 tgtactagtc ttgtgctggt cacagtgtat cttatttatg cattacttgc ttccttgcat    657 gattgtcttt atgcatcccc aatcttaatt gagaccatac ttgtataaga tttttgtaat    717 atctttctgc tattggatat atttattagt taatatattt atttattttt tgctattaat    777 gtatttaatt ttttac                                                    793
```

<210> SEQ ID NO 4
<211> LENGTH: 151
<212> TYPE: PRT
<213> ORGANISM: Homo sapiens

<400> SEQUENCE: 4

```
Met Lys Ala Ser Ser Leu Ala Phe Ser Leu Leu Ser Ala Ala Phe Tyr
  1               5                  10                  15

Leu Leu Trp Thr Pro Ser Thr Gly Leu Lys Thr Leu Asn Leu Gly Ser
             20                  25                  30

Cys Val Ile Ala Thr Asn Leu Gln Glu Ile Arg Asn Gly Phe Ser Asp
         35                  40                  45

Ile Arg Gly Ser Val Gln Ala Lys Asp Gly Asn Ile Asp Ile Arg Ile
     50                  55                  60

Leu Arg Arg Thr Glu Ser Leu Gln Asp Thr Lys Pro Ala Asn Arg Cys
 65                  70                  75                  80

Cys Leu Leu Arg His Leu Leu Arg Leu Tyr Leu Asp Arg Val Phe Lys
                 85                  90                  95

Asn Tyr Gln Thr Pro Asp His Tyr Thr Leu Arg Lys Ile Ser Ser Leu
            100                 105                 110

Ala Asn Ser Phe Leu Thr Ile Lys Lys Asp Leu Arg Leu Cys Leu Glu
        115                 120                 125

Pro Gln Ala Ala Val Val Lys Ala Leu Gly Glu Leu Asp Ile Leu Leu
    130                 135                 140

Gln Trp Met Glu Glu Thr Glu
145                 150
```

<210> SEQ ID NO 5
<211> LENGTH: 253
<212> TYPE: DNA
<213> ORGANISM: Homo sapiens

<400> SEQUENCE: 5

```
ctttgaattc ctagctcctg tggtctccag atttcaggcc taagatgaaa gcctctagtc    60
ttgccttcag ccttctctct gctgcgtttt atctcctatg gactccttcc actggactga   120
agacactcaa tttgggaagc tgtgtgatcg ccacaaacct tcaggaaata cgaaatggat   180
tttctgagat acggggcagt gtgcaagcca aagatggaaa cattgacatc agaatcttaa   240
ggaggactga gtc                                                      253
```

```
<210> SEQ ID NO 6
<211> LENGTH: 24
<212> TYPE: DNA
<213> ORGANISM: Homo sapiens

<400> SEQUENCE: 6
attcctagct cctgtggtct ccag                                           24
```

```
<210> SEQ ID NO 7
<211> LENGTH: 25
<212> TYPE: DNA
<213> ORGANISM: Homo sapiens

<400> SEQUENCE: 7
ctctgctgcg ttttatctcc tatgg                                          25
```

```
<210> SEQ ID NO 8
<211> LENGTH: 22
<212> TYPE: DNA
<213> ORGANISM: Homo sapiens

<400> SEQUENCE: 8
tcccaaattg agtgtcttca gt                                             22
```

```
<210> SEQ ID NO 9
<211> LENGTH: 45
<212> TYPE: DNA
<213> ORGANISM: Homo sapiens

<400> SEQUENCE: 9
cacagcttcc caaattgagt gtcttcagtc cagtggaagg agtcc                    45
```

```
<210> SEQ ID NO 10
<211> LENGTH: 747
<212> TYPE: DNA
<213> ORGANISM: Homo sapiens

<400> SEQUENCE: 10
ttttctgaca tacggggcag tgtgcaagcc aaagatggaa acattgacat cagaatctta    60
aggaggactg agtctttgca agacacaaag cctgcgaatc gatgctgcct cctgcgccat   120
ttgctaagac tctatctgga cagggtattt aaaaactacc agacccctga ccattatact   180
ctccggaaga tcagcagcct cgccaattcc tttcttacca tcaagaagga cctccggctc   240
tgtcatgccc acatgacatg ccattgtggg aggaagcaa tgaagaaata cagccagatt   300
ctgagtcact tgaaaagct ggaacctcag gcagcagttg tgaaggcttt ggggaacta    360
gacattcttc tgcaatggat ggaggagaca gaataggagg aaagtgatgc tgctgctaag   420
aatattcgag gtcaagagct ccagtcttca atacctgcag aggaggcatg accccaaacc   480
accatctctt tactgtacta gtcttgtgct ggtcacagtg tatcttattt atgcattact   540
tgcttccttg catgattgtc tttatgcatc cccaatctta attgagacca tacttgtata   600
agatttttgt aatatctttc tgctattgga tatatttatt agttaatata tttatttatt   660
```

```
ttttgctatt aatgtattta atttttact  tgggcatgaa acttaaaaa  aaattcacaa      720 gattatattt ataacctgac tagagca                                           747
```

<210> SEQ ID NO 11
<211> LENGTH: 614
<212> TYPE: DNA
<213> ORGANISM: Homo sapiens

<400> SEQUENCE: 11

```
ttttctgaca tacggggcag tgtgcaagcc aaagatggaa acattgacat cagaatctta       60
aggaggactg agtctttgca agacacaaag cctgcgaatc gatgctgcct cctgcgccat      120
ttgctaagac tctatctgga cagggtattt aaaaactacc agaccctga  ccattatact      180 ctccggaaga tcagcagcct cgccaattcc tttcttacca tcaagaagga cctccggctc      240
tgtctggaac ctcaggcagc agttgtgaag gctttggggg aactagacat tcttctgcaa      300
tggatggagg agacagaata ggaggaaagt gatgctgctg ctaagaatat tcgaggtcaa      360
gagctccagt cttcaatacc tgcagaggag gcatgacccc aaaccaccat ctctttactg      420
tactagtctt gtgctggtca cagtgtatct tatttatgca ttacttgctt ccttgcatga      480
ttgtctttat gcatccccaa tcttaattga gaccatactt gtataagatt tttgtaatat      540
ctttctgcta ttggatatat ttattagtta atatatttat ttattttttg ctattaatgt      600
atttaatttt ttac                                                         614
```

<210> SEQ ID NO 12
<211> LENGTH: 152
<212> TYPE: PRT
<213> ORGANISM: Homo sapiens

<400> SEQUENCE: 12

```
Leu Lys Thr Leu Asn Leu Gly Ser Cys Val Ile Ala Thr Asn Leu Gln
  1               5                  10                  15

Glu Ile Arg Asn Gly Phe Ser Asp Ile Arg Gly Ser Val Gln Ala Lys
             20                  25                  30

Asp Gly Asn Ile Asp Ile Arg Ile Leu Arg Arg Thr Glu Ser Leu Gln
         35                  40                  45

Asp Thr Lys Pro Ala Asn Arg Cys Cys Leu Leu Arg His Leu Leu Arg
     50                  55                  60

Leu Tyr Leu Asp Arg Val Phe Lys Asn Tyr Gln Thr Pro Asp His Tyr
 65                  70                  75                  80

Thr Leu Arg Lys Ile Ser Ser Leu Ala Asn Ser Phe Leu Thr Ile Lys
                 85                  90                  95

Lys Asp Leu Arg Leu Cys His Ala His Met Thr Cys His Cys Gly Glu
            100                 105                 110

Glu Ala Met Lys Lys Tyr Ser Gln Ile Leu Ser His Phe Glu Lys Leu
        115                 120                 125

Glu Pro Gln Ala Ala Val Val Lys Ala Leu Gly Glu Leu Asp Ile Leu
    130                 135                 140

Leu Gln Trp Met Glu Glu Thr Glu
145                 150
```

<210> SEQ ID NO 13
<211> LENGTH: 127
<212> TYPE: PRT
<213> ORGANISM: Homo sapiens -continued

```
<400> SEQUENCE: 13

Leu Lys Thr Leu Asn Leu Gly Ser Cys Val Ile Ala Thr Asn Leu Gln
  1               5                  10                  15

Glu Ile Arg Asn Gly Phe Ser Asp Ile Arg Gly Ser Val Gln Ala Lys
             20                  25                  30

Asp Gly Asn Ile Asp Ile Arg Ile Leu Arg Arg Thr Glu Ser Leu Gln
         35                  40                  45

Asp Thr Lys Pro Ala Asn Arg Cys Cys Leu Leu Arg His Leu Leu Arg
     50                  55                  60

Leu Tyr Leu Asp Arg Val Phe Lys Asn Tyr Gln Thr Pro Asp His Tyr
 65                  70                  75                  80

Thr Leu Arg Lys Ile Ser Ser Leu Ala Asn Ser Phe Leu Thr Ile Lys
                 85                  90                  95

Lys Asp Leu Arg Leu Cys Leu Glu Pro Gln Ala Ala Val Val Lys Ala
            100                 105                 110

Leu Gly Glu Leu Asp Ile Leu Leu Gln Trp Met Glu Gly Thr Glu
        115                 120                 125

<210> SEQ ID NO 14
<211> LENGTH: 15
<212> TYPE: PRT
<213> ORGANISM: Homo sapiens

<400> SEQUENCE: 14

Ile Ala Thr Asn Leu Gln Glu Ile Arg Asn Gly Phe Ser Asp Ile
  1               5                  10                  15

<210> SEQ ID NO 15
<211> LENGTH: 15
<212> TYPE: PRT
<213> ORGANISM: Homo sapiens

<400> SEQUENCE: 15

Leu Asp Arg Val Phe Lys Asn Tyr Gln Thr Pro Asp His Tyr Thr
  1               5                  10                  15

<210> SEQ ID NO 16
<211> LENGTH: 15
<212> TYPE: PRT
<213> ORGANISM: Homo sapiens

<400> SEQUENCE: 16

Leu Ala Asn Ser Phe Leu Thr Ile Lys Lys Asp Leu Arg Leu Cys
  1               5                  10                  15

<210> SEQ ID NO 17
<211> LENGTH: 15
<212> TYPE: PRT
<213> ORGANISM: Homo sapiens

<400> SEQUENCE: 17

Val Val Lys Ala Leu Gly Glu Leu Asp Ile Leu Leu Gln Trp Met
  1               5                  10                  15

<210> SEQ ID NO 18
<211> LENGTH: 824
<212> TYPE: DNA
<213> ORGANISM: Mus musculus
<220> FEATURE:
<221> NAME/KEY: CDS
<222> LOCATION: (71)...(598)
```

```
<400> SEQUENCE: 18
tgggagacat cgatagccct gattgatctc tttgaatttt cgcttctggt ctccaggatc        60
taggtgtaag atg aaa ggc ttt ggt ctt gcc ttt gga ctg ttc tcc gct         109
         Met Lys Gly Phe Gly Leu Ala Phe Gly Leu Phe Ser Ala
           1               5                  10 gtg ggt ttt ctt ctc tgg act cct tta act ggg ctc aag acc ctc cat        157
Val Gly Phe Leu Leu Trp Thr Pro Leu Thr Gly Leu Lys Thr Leu His
 15                  20                  25 ttg gga agc tgt gtg att act gca aac cta cag gca ata caa aag gaa        205
Leu Gly Ser Cys Val Ile Thr Ala Asn Leu Gln Ala Ile Gln Lys Glu
 30                  35                  40                  45 ttt tct gag att cgg gat agt gtg caa gct gaa gat aca aat att gac        253
Phe Ser Glu Ile Arg Asp Ser Val Gln Ala Glu Asp Thr Asn Ile Asp
                 50                  55                  60 atc aga att tta agg acg act gag tct ttg aaa gac ata aag tct ttg        301
Ile Arg Ile Leu Arg Thr Thr Glu Ser Leu Lys Asp Ile Lys Ser Leu
 65                  70                  75 gat agg tgc tgc ttc ctt cgt cat cta gtg aga ttc tat ctg gac agg        349
Asp Arg Cys Cys Phe Leu Arg His Leu Val Arg Phe Tyr Leu Asp Arg
 80                  85                  90 gta ttc aaa gtc tac cag acc cct gac cac cat acc ctg aga aag atc        397
Val Phe Lys Val Tyr Gln Thr Pro Asp His His Thr Leu Arg Lys Ile
 95                 100                 105 agc agc ctc gcc aac tcc ttt ctt atc atc aag aag gac ctc tca gtc        445
Ser Ser Leu Ala Asn Ser Phe Leu Ile Ile Lys Lys Asp Leu Ser Val
110                 115                 120                 125 tgt cat tct cac atg gca tgt cat tgt ggg gaa gaa gca atg gag aaa        493
Cys His Ser His Met Ala Cys His Cys Gly Glu Glu Ala Met Glu Lys
                130                 135                 140 tac aac caa att ctg agt cac ttc ata gag ttg gaa ctt cag gca gcg        541
Tyr Asn Gln Ile Leu Ser His Phe Ile Glu Leu Glu Leu Gln Ala Ala
                145                 150                 155 gtg gta aag gct ttg gga gaa cta ggc att ctt ctg aga tgg atg gag        589
Val Val Lys Ala Leu Gly Glu Leu Gly Ile Leu Leu Arg Trp Met Glu
160                 165                 170 gag atg cta tagatgaaag tggagaggct gctgagaaca ctcctgtcca               638
Glu Met Leu
        175 agaatctcag acctcagcac catgaagaca tggccccagg tgctggcatt tctactcaag      698 agttccagtc ctcagcacca cgaagatggc ctcaaaccac cacccctttg tgatataact      758 tagtgctagc tatgtgtata ttatttctac attattggct cccttatgtg aatgccttca      818 tgtgtc                                                                 824

<210> SEQ ID NO 19
<211> LENGTH: 176
<212> TYPE: PRT
<213> ORGANISM: Mus musculus

<400> SEQUENCE: 19

Met Lys Gly Phe Gly Leu Ala Phe Gly Leu Phe Ser Ala Val Gly Phe
  1               5                  10                  15

Leu Leu Trp Thr Pro Leu Thr Gly Leu Lys Thr Leu His Leu Gly Ser
             20                  25                  30

Cys Val Ile Thr Ala Asn Leu Gln Ala Ile Gln Lys Glu Phe Ser Glu
         35                  40                  45

Ile Arg Asp Ser Val Gln Ala Glu Asp Thr Asn Ile Asp Ile Arg Ile
     50                  55                  60
```

```
Leu Arg Thr Thr Glu Ser Leu Lys Asp Ile Lys Ser Leu Asp Arg Cys
 65                  70                  75                  80

Cys Phe Leu Arg His Leu Val Arg Phe Tyr Leu Asp Arg Val Phe Lys
                 85                  90                  95

Val Tyr Gln Thr Pro Asp His His Thr Leu Arg Lys Ile Ser Ser Leu
            100                 105                 110

Ala Asn Ser Phe Leu Ile Ile Lys Lys Asp Leu Ser Val Cys His Ser
            115                 120                 125

His Met Ala Cys His Cys Gly Glu Glu Ala Met Glu Lys Tyr Asn Gln
130                 135                 140

Ile Leu Ser His Phe Ile Glu Leu Glu Leu Gln Ala Ala Val Val Lys
145                 150                 155                 160

Ala Leu Gly Glu Leu Gly Ile Leu Leu Arg Trp Met Glu Glu Met Leu
                165                 170                 175
```

<210> SEQ ID NO 20
<211> LENGTH: 152
<212> TYPE: PRT
<213> ORGANISM: Mus musculus

<400> SEQUENCE: 20

```
Leu Lys Thr Leu His Leu Gly Ser Cys Val Ile Thr Ala Asn Leu Gln
  1               5                  10                  15

Ala Ile Gln Lys Glu Phe Ser Glu Ile Arg Asp Ser Val Gln Ala Glu
             20                  25                  30

Asp Thr Asn Ile Asp Ile Arg Ile Leu Arg Thr Thr Glu Ser Leu Lys
             35                  40                  45

Asp Ile Lys Ser Leu Asp Arg Cys Cys Phe Leu Arg His Leu Val Arg
 50                  55                  60

Phe Tyr Leu Asp Arg Val Phe Lys Val Tyr Gln Thr Pro Asp His His
 65                  70                  75                  80

Thr Leu Arg Lys Ile Ser Ser Leu Ala Asn Ser Phe Leu Ile Ile Lys
                 85                  90                  95

Lys Asp Leu Ser Val Cys His Ser His Met Ala Cys His Cys Gly Glu
            100                 105                 110

Glu Ala Met Glu Lys Tyr Asn Gln Ile Leu Ser His Phe Ile Glu Leu
            115                 120                 125

Glu Leu Gln Ala Ala Val Val Lys Ala Leu Gly Glu Leu Gly Ile Leu
130                 135                 140

Leu Arg Trp Met Glu Glu Met Leu
145                 150
```

<210> SEQ ID NO 21
<211> LENGTH: 16
<212> TYPE: PRT
<213> ORGANISM: Mus musculus

<400> SEQUENCE: 21

```
Ile Thr Ala Asn Leu Gln Ala Ile Gln Lys Glu Phe Ser Glu Ile Arg
  1               5                  10                  15
```

<210> SEQ ID NO 22
<211> LENGTH: 15
<212> TYPE: PRT
<213> ORGANISM: Mus musculus

<400> SEQUENCE: 22

```
Leu Asp Arg Val Phe Lys Val Tyr Gln Thr Pro Asp His His Thr
 1               5                  10                  15

<210> SEQ ID NO 23
<211> LENGTH: 15
<212> TYPE: PRT
<213> ORGANISM: Mus musculus

<400> SEQUENCE: 23

Leu Ala Asn Ser Phe Leu Ile Ile Lys Lys Asp Leu Ser Val Cys
 1               5                  10                  15

<210> SEQ ID NO 24
<211> LENGTH: 15
<212> TYPE: PRT
<213> ORGANISM: Mus muculus

<400> SEQUENCE: 24

Val Val Lys Ala Leu Gly Glu Leu Gly Ile Leu Leu Arg Trp Met
 1               5                  10                  15

<210> SEQ ID NO 25
<211> LENGTH: 144
<212> TYPE: PRT
<213> ORGANISM: Mus muculus

<400> SEQUENCE: 25

Cys Val Ile Thr Ala Asn Leu Gln Ala Ile Gln Lys Glu Phe Ser Glu
 1               5                  10                  15

Ile Arg Asp Ser Val Gln Ala Glu Asp Thr Asn Ile Asp Ile Arg Ile
                20                  25                  30

Leu Arg Thr Thr Glu Ser Leu Lys Asp Ile Lys Ser Leu Asp Arg Cys
            35                  40                  45

Cys Phe Leu Arg His Leu Val Arg Phe Tyr Leu Asp Arg Val Phe Lys
        50                  55                  60

Val Tyr Gln Thr Pro Asp His His Thr Leu Arg Lys Ile Ser Ser Leu
65                  70                  75                  80

Ala Asn Ser Phe Leu Ile Ile Lys Lys Asp Leu Ser Val Cys His Ser
                85                  90                  95

His Met Ala Cys His Cys Gly Glu Glu Ala Met Glu Lys Tyr Asn Gln
            100                 105                 110

Ile Leu Ser His Phe Ile Glu Leu Glu Leu Gln Ala Ala Val Val Lys
        115                 120                 125

Ala Leu Gly Glu Leu Gly Ile Leu Leu Arg Trp Met Glu Glu Met Leu
    130                 135                 140

<210> SEQ ID NO 26
<211> LENGTH: 144
<212> TYPE: PRT
<213> ORGANISM: Homo sapiens

<400> SEQUENCE: 26

Cys Val Ile Ala Thr Asn Leu Gln Glu Ile Arg Asn Gly Phe Ser Asp
 1               5                  10                  15

Ile Arg Gly Ser Val Gln Ala Lys Asp Gly Asn Ile Asp Ile Arg Ile
                20                  25                  30

Leu Arg Arg Thr Glu Ser Leu Gln Asp Thr Lys Pro Ala Asn Arg Cys
            35                  40                  45

Cys Leu Leu Arg His Leu Leu Arg Leu Tyr Leu Asp Arg Val Phe Lys
        50                  55                  60
```

```
Asn Tyr Gln Thr Pro Asp His Tyr Thr Leu Arg Lys Ile Ser Ser Leu
 65                  70                  75                  80

Ala Asn Ser Phe Leu Thr Ile Lys Lys Asp Leu Arg Leu Cys His Ala
                 85                  90                  95

His Met Thr Cys His Cys Gly Glu Glu Ala Met Lys Lys Tyr Ser Gln
            100                 105                 110

Ile Leu Ser His Phe Glu Lys Leu Glu Pro Gln Ala Ala Val Val Lys
        115                 120                 125

Ala Leu Gly Glu Leu Asp Ile Leu Leu Gln Trp Met Glu Glu Thr Glu
    130                 135                 140

<210> SEQ ID NO 27
<211> LENGTH: 38
<212> TYPE: PRT
<213> ORGANISM: Homo sapiens

<400> SEQUENCE: 27

Cys Gly Glu Glu Ala Met Lys Lys Tyr Ser Gln Ile Leu Ser His Phe
  1               5                  10                  15

Glu Lys Leu Glu Pro Gln Ala Ala Val Val Lys Ala Leu Gly Glu Leu
                 20                  25                  30

Asp Ile Leu Leu Gln Trp
            35

<210> SEQ ID NO 28
<211> LENGTH: 71
<212> TYPE: PRT
<213> ORGANISM: Homo sapiens

<400> SEQUENCE: 28

Ile Ala Thr Asn Leu Gln Glu Ile Arg Asn Gly Phe Ser Asp Ile Arg
  1               5                  10                  15

Gly Ser Val Gln Ala Lys Asp Gly Asn Ile Asp Ile Arg Ile Leu Arg
                 20                  25                  30

Arg Thr Glu Ser Leu Gln Asp Thr Lys Pro Ala Asn Arg Cys Cys Leu
            35                  40                  45

Leu Arg His Leu Leu Arg Leu Tyr Leu Asp Arg Val Phe Lys Asn Tyr
     50                  55                  60

Gln Thr Pro Asp His Tyr Thr
 65                  70

<210> SEQ ID NO 29
<211> LENGTH: 92
<212> TYPE: PRT
<213> ORGANISM: Homo sapiens

<400> SEQUENCE: 29

Ile Ala Thr Asn Leu Gln Glu Ile Arg Asn Gly Phe Ser Asp Ile Arg
  1               5                  10                  15

Gly Ser Val Gln Ala Lys Asp Gly Asn Ile Asp Ile Arg Ile Leu Arg
                 20                  25                  30

Arg Thr Glu Ser Leu Gln Asp Thr Lys Pro Ala Asn Arg Cys Cys Leu
            35                  40                  45

Leu Arg His Leu Leu Arg Leu Tyr Leu Asp Arg Val Phe Lys Asn Tyr
     50                  55                  60

Gln Thr Pro Asp His Tyr Thr Leu Arg Lys Ile Ser Ser Leu Ala Asn
 65                  70                  75                  80
```

Ser Phe Leu Thr Ile Lys Lys Asp Leu Arg Leu Cys
            85                  90

<210> SEQ ID NO 30
<211> LENGTH: 82
<212> TYPE: PRT
<213> ORGANISM: Homo sapiens

<400> SEQUENCE: 30

Leu Asp Arg Val Phe Lys Asn Tyr Gln Thr Pro Asp His Tyr Thr Leu
1               5                   10                  15

Arg Lys Ile Ser Ser Leu Ala Asn Ser Phe Leu Thr Ile Lys Lys Asp
            20                  25                  30

Leu Arg Leu Cys His Ala His Met Thr Cys His Cys Gly Glu Glu Ala
        35                  40                  45

Met Lys Lys Tyr Ser Gln Ile Leu Ser His Phe Glu Lys Leu Glu Pro
    50                  55                  60

Gln Ala Ala Val Val Lys Ala Leu Gly Glu Leu Asp Ile Leu Leu Gln
65                  70                  75                  80

Trp Met

<210> SEQ ID NO 31
<211> LENGTH: 36
<212> TYPE: PRT
<213> ORGANISM: Homo sapiens

<400> SEQUENCE: 31

Leu Asp Arg Val Phe Lys Asn Tyr Gln Thr Pro Asp His Tyr Thr Leu
1               5                   10                  15

Arg Lys Ile Ser Ser Leu Ala Asn Ser Phe Leu Thr Ile Lys Lys Asp
            20                  25                  30

Leu Arg Leu Cys
        35

<210> SEQ ID NO 32
<211> LENGTH: 61
<212> TYPE: PRT
<213> ORGANISM: Homo sapiens

<400> SEQUENCE: 32

Leu Ala Asn Ser Phe Leu Thr Ile Lys Lys Asp Leu Arg Leu Cys His
1               5                   10                  15

Ala His Met Thr Cys His Cys Gly Glu Glu Ala Met Lys Lys Tyr Ser
            20                  25                  30

Gln Ile Leu Ser His Phe Glu Lys Leu Glu Pro Gln Ala Ala Val Val
        35                  40                  45

Lys Ala Leu Gly Glu Leu Asp Ile Leu Leu Gln Trp Met
    50                  55                  60

<210> SEQ ID NO 33
<211> LENGTH: 756
<212> TYPE: DNA
<213> ORGANISM: Mus musculus
<220> FEATURE:
<221> NAME/KEY: CDS
<222> LOCATION: (71)...(532)

<400> SEQUENCE: 33
tgggagacat cgatagccct gattgatctc tttgaatttt cgcttctggt ctccaggatc      60
taggtgtaag atg aaa ggc ttt ggt ctt gcc ttt gga ctg ttc tcc gct        109

```
                Met Lys Gly Phe Gly Leu Ala Phe Gly Leu Phe Ser Ala
                  1               5                  10 gtg ggt ttt ctt ctc tgg act cct tta act ggg ctc aag acc ctc cat          157
Val Gly Phe Leu Leu Trp Thr Pro Leu Thr Gly Leu Lys Thr Leu His
 15              20                  25 ttg gga agc tgt gtg att act gca aac cta cag gca ata caa aag gaa          205
Leu Gly Ser Cys Val Ile Thr Ala Asn Leu Gln Ala Ile Gln Lys Glu
 30              35                  40                  45 ttt tct gag att cgg gat agt gtg tct ttg gat agg tgc tgc ttc ctt          253
Phe Ser Glu Ile Arg Asp Ser Val Ser Leu Asp Arg Cys Cys Phe Leu
                 50                  55                  60 cgt cat cta gtg aga ttc tat ctg gac agg gta ttc aaa gtc tac cag          301
Arg His Leu Val Arg Phe Tyr Leu Asp Arg Val Phe Lys Val Tyr Gln
             65                  70                  75 acc cct gac cac cat acc ctg aga aag atc agc agc ctc gcc aac tcc          349
Thr Pro Asp His His Thr Leu Arg Lys Ile Ser Ser Leu Ala Asn Ser
         80                  85                  90 ttt ctt atc atc aag aag gac ctc tca gtc tgt cat tct cac atg gca          397
Phe Leu Ile Ile Lys Lys Asp Leu Ser Val Cys His Ser His Met Ala
     95                  100                 105 tgt cat tgt ggg gaa gaa gca atg gag aaa tac aac caa att ctg agt          445
Cys His Cys Gly Glu Glu Ala Met Glu Lys Tyr Asn Gln Ile Leu Ser
110                 115                 120                 125 cac ttc ata gag ttg gaa ctt cag gca gcg gtg gta aag gct ttg gga          493
His Phe Ile Glu Leu Glu Leu Gln Ala Ala Val Val Lys Ala Leu Gly
                130                 135                 140 gaa cta ggc att ctt ctg aga tgg atg gag gag atg cta tagatgaaag           542
Glu Leu Gly Ile Leu Leu Arg Trp Met Glu Glu Met Leu
                145                 150 tggataggct gctgagaaca ctcctgtcca agaatctcag acctcagcac catgaagaca        602
tggccccagg tgctggcatt tctactcaag agttccagtc ctcagcacca cgaagatggc        662
ctcaaaccac caccccttg tgatataact tagtgctagc tatgtgtata ttatttctac         722
attattggct cccttatgtg aatgccttca tgtg                                    756

<210> SEQ ID NO 34
<211> LENGTH: 154
<212> TYPE: PRT
<213> ORGANISM: Mus musculus

<400> SEQUENCE: 34

Met Lys Gly Phe Gly Leu Ala Phe Gly Leu Phe Ser Ala Val Gly Phe
  1               5                  10                  15

Leu Leu Trp Thr Pro Leu Thr Gly Leu Lys Thr Leu His Leu Gly Ser
                 20                  25                  30

Cys Val Ile Thr Ala Asn Leu Gln Ala Ile Gln Lys Glu Phe Ser Glu
             35                  40                  45

Ile Arg Asp Ser Val Ser Leu Asp Arg Cys Cys Phe Leu Arg His Leu
         50                  55                  60

Val Arg Phe Tyr Leu Asp Arg Val Phe Lys Val Tyr Gln Thr Pro Asp
 65                  70                  75                  80

His His Thr Leu Arg Lys Ile Ser Ser Leu Ala Asn Ser Phe Leu Ile
                 85                  90                  95

Ile Lys Lys Asp Leu Ser Val Cys His Ser His Met Ala Cys His Cys
            100                 105                 110

Gly Glu Glu Ala Met Glu Lys Tyr Asn Gln Ile Leu Ser His Phe Ile
        115                 120                 125
```

```
Glu Leu Glu Leu Gln Ala Ala Val Lys Ala Leu Gly Glu Leu Gly
    130                 135                 140
Ile Leu Leu Arg Trp Met Glu Glu Met Leu
145                 150

<210> SEQ ID NO 35
<211> LENGTH: 130
<212> TYPE: PRT
<213> ORGANISM: Mus musculus

<400> SEQUENCE: 35

Leu Lys Thr Leu His Leu Gly Ser Cys Val Ile Thr Ala Asn Leu Gln
  1               5                  10                  15
Ala Ile Gln Lys Glu Phe Ser Glu Ile Arg Asp Ser Val Ser Leu Asp
             20                  25                  30
Arg Cys Cys Phe Leu Arg His Leu Val Arg Phe Tyr Leu Asp Arg Val
         35                  40                  45
Phe Lys Val Tyr Gln Thr Pro Asp His His Thr Leu Arg Lys Ile Ser
     50                  55                  60
Ser Leu Ala Asn Ser Phe Leu Ile Ile Lys Lys Asp Leu Ser Val Cys
 65                  70                  75                  80
His Ser His Met Ala Cys His Cys Gly Glu Glu Ala Met Glu Lys Tyr
                 85                  90                  95
Asn Gln Ile Leu Ser His Phe Ile Glu Leu Glu Leu Gln Ala Ala Val
            100                 105                 110
Val Lys Ala Leu Gly Glu Leu Gly Ile Leu Leu Arg Trp Met Glu Glu
        115                 120                 125
Met Leu
    130

<210> SEQ ID NO 36
<211> LENGTH: 27
<212> TYPE: DNA
<213> ORGANISM: Homo sapiens

<400> SEQUENCE: 36
agattctatc tggacagggt attcaaa                                     27

<210> SEQ ID NO 37
<211> LENGTH: 17
<212> TYPE: DNA
<213> ORGANISM: Homo sapiens

<400> SEQUENCE: 37
gcgaggctga tctttct                                                17

<210> SEQ ID NO 38
<211> LENGTH: 25
<212> TYPE: DNA
<213> ORGANISM: Mus musculis

<400> SEQUENCE: 38
tggcgaggct gctgatcttt ctcag                                       25

<210> SEQ ID NO 39
<211> LENGTH: 25
<212> TYPE: DNA
<213> ORGANISM: Mus musculis

<400> SEQUENCE: 39
```

```
ctttatgtct tcaaagact cagtc                                              25

<210> SEQ ID NO 40
<211> LENGTH: 26
<212> TYPE: DNA
<213> ORGANISM: Mus musculis

<400> SEQUENCE: 40
catcagaatt ttaaggacga ctgagt                                            26

<210> SEQ ID NO 41
<211> LENGTH: 25
<212> TYPE: DNA
<213> ORGANISM: Mus musculis

<400> SEQUENCE: 41
ggtggtcagg ggtctggtag acttt                                             25

<210> SEQ ID NO 42
<211> LENGTH: 23
<212> TYPE: DNA
<213> ORGANISM: Mus musculis

<400> SEQUENCE: 42
ggtgcatatt cctggtggct aga                                               23

<210> SEQ ID NO 43
<211> LENGTH: 25
<212> TYPE: DNA
<213> ORGANISM: Mus musculis

<400> SEQUENCE: 43
attgcagtgt aagggaatac agaga                                             25
```

ANTIBODY TO MAMMALIAN CYTOKINE-LIKE POLYPEPTIDE-10

The present application is a continuation of U.S. patent application Ser. No. 10/413,661, filed Apr. 15, 2003, now U.S. Pat. No. 7,115,714 incorporated herein by reference; which is a continuation of U.S. patent application Ser. No. 09/313,458, filed May 17, 1999, issued as U.S. Pat. No. 6,576,743 on Jun. 10, 2003, which is a continuation-in-part of U.S. patent application Ser. No. 09/199,586, filed Nov. 25, 1998, now abandoned, which claims the benefit under 35 U.S.C. §119 (e) of U.S. Provisional Application No. 60/066,597, filed Nov. 26, 1997.

BACKGROUND OF THE INVENTION

Proliferation and differentiation of cells of multicellular organisms are controlled by hormones and polypeptide growth factors. These diffusable molecules allow cells to communicate with each other and act in concert to form cells and organs, and to repair and regenerate damaged tissue. Examples of hormones and growth factors include the steroid hormones (e.g. estrogen, testosterone), parathyroid hormone, follicle stimulating hormone, the interleukins, platelet derived growth factor (PDGF), epidermal growth factor (EGF), granulocyte-macrophage colony stimulating factor (GM-CSF), erythropoietin (EPO) and calcitonin.

Hormones and growth factors influence cellular metabolism by binding to proteins. Proteins may be integral membrane proteins that are linked to signaling pathways within the cell, such as second messenger systems. Other classes of proteins are soluble molecules.

Of particular interest are cytokines, molecules that promote the proliferation and/or differentiation of cells. Examples of cytokines include erythropoietin (EPO), which stimulates the development of red blood cells; thrombopoietin (TPO), which stimulates development of cells of the megakaryocyte lineage; and granulocyte-colony stimulating factor (G-CSF), which stimulates development of neutrophils. These cytokines are useful in restoring normal blood cell levels in patients suffering from anemia or receiving chemotherapy for cancer. The demonstrated in vivo activities of these cytokines illustrates the enormous clinical potential of, and need for, other cytokines, cytokine agonists, and cytokine antagonists.

SUMMARY OF THE INVENTION

The present invention addresses this need by providing a novel polypeptide and related compositions and methods. Within one aspect, the present invention provides an isolated polynucleotide encoding a mammalian four alpha helix cytokine termed Zcyto10. The human Zcyto10 polypeptide is comprised of a sequence of 176 amino acids with the initial Met as shown in SEQ ID NO:1 and SEQ ID NO:2. It is believed that amino residues 1–24 are signal sequence, and the mature Zcyto10 polypeptide is represented by the amino acid sequence comprised of residues 25, a leucine, through amino acid residue 176, a glutamic acid residue, also defined by SEQ ID NO:12. Another embodiment of the present invention is defined by the sequences of SEQ ID NO: 3 and SEQ ID NO: 4. The polypeptide of SEQ ID NO: 4 is comprised of 151 amino acid residues wherein amino acids 1–24 comprise a signal sequence and the mature sequence is comprised of amino acid residues 25, a leucine, through amino acid 151 a glutamic acid, also defined by SEQ ID NO:13. Another active variant is comprised of amino acid residues 33, a cysteine, through amino acid residue 176 of SEQ ID NO:2. This variant is also defined by SEQ ID NO:26.

Mouse Zcyto10 is also a polypeptide comprised of 176 amino acid residues as defined by SEQ ID NOs: 18 and 19. Mouse Zcyto10 has a signal sequence extending from amino acid residue 1, a methionine, extending to and including amino acid residue 24, a glycine of SEQ ID NO:19. Thus, the mature mouse Zcyto10 extends from amino acid residue 25, a leucine, to and including amino acid residue 176 a leucine of SEQ ID NO:19, also defined by SEQ ID NO:20. Another active variant is believed to extend from amino acid 33, a cysteine, through amino acid 176, of SEQ ID NO:19. This variant is also defined by SEQ ID NO:25. Within an additional embodiment, the polypeptide further comprises an affinity tag.

A variant of mouse Zcyto10 is defined by SEQ ID NOs: 33 and 34. This variant is 154 amino acid residues in length and has a signal sequence extending from amino acid residue 1, a methionine, to and including amino acid residue 24, a glycine, of SEQ ID NO:34. Thus, the mature sequence extends from amino acid residue 25, a leucine, to and including amino acid residue 154, a leucine, of SEQ ID NO:34. The mature sequence is also defined by SEQ ID NO:35.

Within a second aspect of the invention there is provided an expression vector comprising (a) a transcription promoter; (b) a DNA segment encoding Zcyto10 polypeptide, and (c) a transcription terminator, wherein the promoter, DNA segment, and terminator are operably linked.

Within a third aspect of the invention there is provided a cultured eukaryotic or prokaryotic cell into which has been introduced an expression vector as disclosed above, wherein said cell expresses a polypeptide encoded by the DNA segment.

Within a further aspect of the invention there is provided a chimeric polypeptide consisting essentially of a first portion and a second portion joined by a peptide bond. The first portion of the chimeric polypeptide consists essentially of (a) a Zcyto10 polypeptide as shown in SEQ ID NO: 2 (b) allelic variants of SEQ ID NO:2, SEQ ID NO:4, SEQ ID NO:12, SEQ ID NO:13, SEQ ID NO:19, SEQ ID NO:20, SEQ ID NO:25, SEQ ID NO:26 SEQ ID NO:34 or SEQ ID NO:35; and (c) protein polypeptides that are at least 90% identical to (a) or (b). The second portion of the chimeric polypeptide consists essentially of another polypeptide such as an affinity tag. Within one embodiment the affinity tag is an immunoglobulin $F_c$ polypeptide. The invention also provides expression vectors encoding the chimeric polypeptides and host cells transfected to produce the chimeric polypeptides.

Within an additional aspect of the invention there is provided an antibody that specifically binds to a Zcyto10 polypeptide as disclosed above, and also an anti-idiotypic antibody which neutralizes the antibody to a Zcyto10 polypeptide.

Within another aspect of the present invention there is provided a pharmaceutical composition comprising purified Zcyto10 polypeptide in combination with a pharmaceutically acceptable vehicle. Such compositions may be useful for modulating of cell proliferation, cell differentiation or cytokine production in the prevention or treatment of conditions characterized by improper cell proliferation, cell differentiation or cytokine production, as are further discussed herein. More specifically, Zcyto10 polypeptide may be useful in the prevention or treatment of autoimmune diseases by inhibiting a cellular immune response. Autoimmune diseases which may be amenable to Zcyto10 treatment include IDDM, multiple sclerosis, rheumatoid arthritis and the like. Also, Zcyto10 polypeptides of the present invention may be useful in inhibiting cancer cell growth or proliferation.

Zcyto10 polypeptides of the present invention may also stimulate the immune system to better combat microbial or viral infections. In particular, Zcyto10 can be administered systemically to increase platelet production by an individual. Moreover, Zcyto10 polypeptides of the present invention may be used in trachea-specific or tracheobronchial-specific applications, such as in the maintenance or wound repair of the tracheobronchial epithelium or cells underlying the same, in regulating mucous production or mucocilary clearance of debris or in treatment of asthma, bronchitis or other diseases of the tracheobronchial tract. It may also enhance wound healing and promote regeneration of affected tissues which may be especially useful in the treatment of periodontal disease. Furthermore, Zcyto10 polypeptides can be used to treat skin conditions such as psoriasis, eczema and dry skin in general.

An additional embodiment of the present invention relates to a peptide or polypeptide which has the amino acid sequence of an epitope-bearing portion of a Zcyto10 polypeptide having an amino acid sequence described above. Peptides or polypeptides having the amino acid sequence of an epitope-bearing portion of a Zcyto10 polypeptide of the present invention include portions of such polypeptides with at least nine, preferably at least 15 and more preferably at least 30 to 50 amino acids, although epitope-bearing polypeptides of any length up to and including the entire amino acid sequence of a polypeptide of the present invention described above are also included in the present invention. Also claimed are any of these polypeptides that are fused to another polypeptide or carrier molecule. Such epitope variants include but are not limited to SEQ ID NOs: 25–32. Antibodies produced from these epitope-bearing portions of Zcyto10 can be used in purifying Zcyto10 from cell culture medium.

These and other aspects of the invention will become evident upon reference to the following detailed description and the attached drawing.

DETAILED DESCRIPTION OF THE INVENTION

The teachings of all the references cited herein are incorporated in their entirety by reference.

Prior to setting forth the invention in detail, it may be helpful to the understanding thereof to define the following terms:

The term "affinity tag" is used herein to denote a polypeptide segment that can be attached to a second polypeptide to provide for purification or detection of the second polypeptide or provide sites for attachment of the second polypeptide to a substrate. In principal, any peptide or protein for which an antibody or other specific binding agent is available can be used as an affinity tag. Affinity tags include a polyhistidine tract, protein A, Nilsson et al., *EMBO J.* 4:1075 (1985); Nilsson et al., *Methods Enzymol.* 198:3 (1991), glutathione S transferase, Smith and Johnson, *Gene* 67:31 (1988), Glu-Glu affinity tag, Grussenmeyer et al., *Proc. Natl. Acad. Sci. USA* 82:7952–4 (1985), substance P, Flag™ peptide, Hopp et al., *Biotechnology* 6:1204–1210 (1988), streptavidin binding peptide, or other antigenic epitope or binding domain. See, in general, Ford et al., *Protein Expression and Purification* 2: 95–107 (1991). DNAs encoding affinity tags are available from commercial suppliers (e.g., Pharmacia Biotech, Piscataway, N.J.).

The term "allelic variant" is used herein to denote any of two or more alternative forms of a gene occupying the same chromosomal locus. Allelic variation arises naturally through mutation, and may result in phenotypic polymorphism within populations. Gene mutations can be silent (no change in the encoded polypeptide) or may encode polypeptides having altered amino acid sequence. The term allelic variant is also used herein to denote a protein encoded by an allelic variant of a gene.

The terms "amino-terminal" and "carboxyl-terminal" are used herein to denote positions within polypeptides. Where the context allows, these terms are used with reference to a particular sequence or portion of a polypeptide to denote proximity or relative position. For example, a certain sequence positioned carboxyl-terminal to a reference sequence within a polypeptide is located proximal to the carboxyl terminus of the reference sequence, but is not necessarily at the carboxyl terminus of the complete polypeptide.

The term "complement/anti-complement pair" denotes non-identical moieties that form a non-covalently associated, stable pair under appropriate conditions. For instance, biotin and avidin (or streptavidin) are prototypical members of a complement/anti-complement pair. Other exemplary complement/anti-complement pairs include receptor/ligand pairs, antibody/antigen (or hapten or epitope) pairs, sense/antisense polynucleotide pairs, and the like. Where subsequent dissociation of the complement/anti-complement pair is desirable, the complement/anti-complement pair preferably has a binding affinity of $<10^9$ $M^{-1}$.

The term "complements of a polynucleotide molecule" is a polynucleotide molecule having a complementary base sequence and reverse orientation as compared to a reference sequence. For example, the sequence 5' ATGCACGGG 3' is complementary to 5' CCCGTGCAT 3'.

The term "contig" denotes a polynucleotide that has a contiguous stretch of identical or complementary sequence to another polynucleotide. Contiguous sequences are said to "overlap" a given stretch of polynucleotide sequence either in their entirety or along a partial stretch of the polynucleotide. For example, representative contigs to the polynucleotide sequence 5'-ATGGCTTAGCTT-3' are 5'-TAGCT-Tgagtct-3' and 3'-gtcgacTACCGA-5'.

The term "degenerate nucleotide sequence" denotes a sequence of nucleotides that includes one or more degenerate codons (as compared to a reference polynucleotide molecule that encodes a polypeptide). Degenerate codons contain different triplets of nucleotides, but encode the same amino acid residue (i.e., GAU and GAC triplets each encode Asp).

The term "expression vector" is used to denote a DNA molecule, linear or circular, that comprises a segment encoding a polypeptide of interest operably linked to additional segments that provide for its transcription. Such additional segments include promoter and terminator sequences, and may also include one or more origins of replication, one or more selectable markers, an enhancer, a polyadenylation signal, etc. Expression vectors are generally derived from plasmid or viral DNA, or may contain elements of both.

The term "isolated", when applied to a polynucleotide, denotes that the polynucleotide has been removed from its natural genetic milieu and is thus free of other extraneous or unwanted coding sequences, and is in a form suitable for use within genetically engineered protein production systems. Such isolated molecules are those that are separated from their natural environment and include cDNA and genomic clones. Isolated DNA molecules of the present invention are free of other genes with which they are ordinarily associated, but may include naturally occurring 5' and 3' untranslated regions such as promoters and terminators. The identification of associated regions will be evident to one of ordinary skill in the art (see for example, Dynan and Tijan, *Nature* 316:774–78 (1985).

An "isolated" polypeptide or protein is a polypeptide or protein that is found in a condition other than its native environment, such as apart from blood and animal tissue. In a preferred form, the isolated polypeptide is substantially free of other polypeptides, particularly other polypeptides of animal origin. It is preferred to provide the polypeptides in a highly purified form, i.e. greater than 95% pure, more preferably greater than 99% pure. When used in this context, the term "isolated" does not exclude the presence of the same polypeptide in alternative physical forms, such as dimers or alternatively glycosylated or derivatized forms.

The term "operably linked", when referring to DNA segments, indicates that the segments are arranged so that they function in concert for their intended purposes, e.g., transcription initiates in the promoter and proceeds through the coding segment to the terminator.

The term "ortholog" denotes a polypeptide or protein obtained from one species that is the functional counterpart of a polypeptide or protein from a different species. Sequence differences among orthologs are the result of speciation.

"Paralogs" are distinct but structurally related proteins made by an organism. Paralogs are believed to arise through gene duplication. For example, a-globin, b-globin, and myoglobin are paralogs of each other.

A "polynucleotide" is a single- or double-stranded polymer of deoxyribonucleotide or ribonucleotide bases read from the 5' to the 3' end. Polynucleotides include RNA and DNA, and may be isolated from natural sources, synthesized in vitro, or prepared from a combination of natural and synthetic molecules. Sizes of polynucleotides are expressed as base pairs (abbreviated "bp"), nucleotides ("nt"), or kilobases ("kb"). Where the context allows, the latter two terms may describe polynucleotides that are single-stranded or double-stranded. When the term is applied to double-stranded molecules it is used to denote overall length and will be understood to be equivalent to the term "base pairs". It will be recognized by those skilled in the art that the two strands of a double-stranded polynucleotide may differ slightly in length and that the ends thereof may be staggered as a result of enzymatic cleavage; thus all nucleotides within a double-stranded polynucleotide molecule may not be paired. Such unpaired ends will in general not exceed 20 nt in length.

A "polypeptide" is a polymer of amino acid residues joined by peptide bonds, whether produced naturally or synthetically. Polypeptides of less than about 10 amino acid residues are commonly referred to as "peptides".

The term "promoter" is used herein for its art-recognized meaning to denote a portion of a gene containing DNA sequences that provide for the binding of RNA polymerase and initiation of transcription. Promoter sequences are commonly, but not always, found in the 5' non-coding regions of genes.

A "protein" is a macromolecule comprising one or more polypeptide chains. A protein may also comprise non-peptidic components, such as carbohydrate groups. Carbohydrates and other non-peptidic substituents may be added to a protein by the cell in which the protein is produced, and will vary with the type of cell. Proteins are defined herein in terms of their amino acid backbone structures; substituents such as carbohydrate groups are generally not specified, but may be present nonetheless.

The term "receptor" denotes a cell-associated protein that binds to a bioactive molecule (i.e., a ligand) and mediates the effect of the ligand on the cell. Membrane-bound receptors are characterized by a multi-domain structure comprising an extracellular ligand-binding domain and an intracellular effector domain that is typically involved in signal transduction. Binding of ligand to receptor results in a conformational change in the receptor that causes an interaction between the effector domain and other molecule(s) in the cell. This interaction in turn leads to an alteration in the metabolism of the cell. Metabolic events that are linked to receptor-ligand interactions include gene transcription, phosphorylation, dephosphorylation, increases in cyclic AMP production, mobilization of cellular calcium, mobilization of membrane lipids, cell adhesion, hydrolysis of inositol lipids and hydrolysis of phospholipids. In general, receptors can be membrane bound, cytosolic or nuclear; monomeric (e.g., thyroid stimulating hormone receptor, beta-adrenergic receptor) or multimeric (e.g., PDGF receptor, growth hormone receptor, IL-3 receptor, GM-CSF receptor, G-CSF receptor, erythropoietin receptor and IL-6 receptor).

The term "secretory signal sequence" denotes a DNA sequence that encodes a polypeptide (a "secretory peptide") that, as a component of a larger polypeptide, directs the larger polypeptide through a secretory pathway of a cell in which it is synthesized. The larger polypeptide is commonly cleaved to remove the secretory peptide during transit through the secretory pathway.

The term "splice variant" is used herein to denote alternative forms of RNA transcribed from a gene. Splice variation arises naturally through use of alternative splicing sites within a transcribed RNA molecule, or less commonly between separately transcribed RNA molecules, and may result in several mRNAs transcribed from the same gene. Splice variants may encode polypeptides having altered amino acid sequence. The term splice variant is also used herein to denote a protein encoded by a splice variant of an mRNA transcribed from a gene.

Molecular weights and lengths of polymers determined by imprecise analytical methods (e.g., gel electrophoresis) will be understood to be approximate values. When such a value is expressed as "about" X or "approximately" X, the stated value of X will be understood to be accurate to ±10%.

It is believed that Zcyto10 is of a member of the IL-10 subfamily of cytokines. Other members of this group include MDA-7, IL-19, and KFF. Conserved amino acids in the helix D of Zcyto10 can be used as a tool to identify new family members. Helix D is the most highly conserved having about 32% identity with the helix D of IL-10. For instance, reverse transcription-polymerase chain reaction (RT-PCR) can be used to amplify sequences encoding the conserved [the domain, region or motif from above] from RNA obtained from a variety of tissue sources or cell lines. In particular, highly degenerate primers designed from the Zcyto10 sequences are useful for this purpose.

Within preferred embodiments of the invention the isolated polynucleotides will hybridize to similar sized regions of SEQ ID NO:1, SEQ ID NO:3, SEQ ID NO:18, SEQ ID NO:33 or a sequence complementary thereto, under stringent conditions. In general, stringent conditions are selected to be about 5° C. lower than the thermal melting point ($T_m$) for the specific sequence at a defined ionic strength and pH.

The T$_m$ is the temperature (under defined ionic strength and pH) at which 50% of the target sequence hybridizes to a perfectly matched probe. Typical stringent conditions are those in which the salt concentration is about 0.02 M or less at pH 7 and the temperature is at least about 60° C. As previously noted, the isolated polynucleotides of the present invention include DNA and RNA. Methods for isolating DNA and RNA are well known in the art. Total RNA can be prepared using guanidine HCl extraction followed by isolation by centrifugation in a CsCl gradient [Chirgwin et al., *Biochemistry* 18:52–94, (1979)]. Poly (A)$^+$ RNA is prepared from total RNA using the method of Aviv and Leder, *Proc. Natl. Acad. Sci. USA* 69:1408–1412 (1972). Complementary DNA (cDNA) is prepared from poly(A)$^+$ RNA using known methods. Polynucleotides encoding Zcyto10 polypeptides are then identified and isolated by, for example, hybridization or PCR.

Additionally, the polynucleotides of the present invention can be synthesized using a DNA synthesizer. Currently the method of choice is the phosphoramidite method. If chemically synthesized double stranded DNA is required for an application such as the synthesis of a gene or a gene fragment, then each complementary strand is made separately. The production of short genes (60 to 80 bp) is technically straightforward and can be accomplished by synthesizing the complementary strands and then annealing them. For the production of longer genes (>300 bp), however, special strategies must be invoked, because the coupling efficiency of each cycle during chemical DNA synthesis is seldom 100%. To overcome this problem, synthetic genes (double-stranded) are assembled in modular form from single-stranded fragments that are from 20 to 100 nucleotides in length. See Glick, Bernard R. and Jack J. Pasternak, *Molecular Biotechnology, Principles & Applications of Recombinant DNA,* (ASM Press, Washington, D.C. 1994), Itakura, K. et al. Synthesis and use of synthetic oligonucleotides. *Annu. Rev. Biochem.* 53: 323–356 (1984), and Climie, S. et al. Chemical synthesis of the thymidylate synthase gene. *Proc. Natl. Acad. Sci. USA* 87 :633–637 (1990).

Those skilled in the art will recognize that the sequences disclosed in SEQ ID NOs:1, 2, 3 and 4 represent a two alleles of the human, and SEQ ID NOs:18, 19, 33 and 34 represent two alleles of the mouse. Additional allelic variants of these sequences can be cloned by probing cDNA or genomic libraries from different individuals according to standard procedures. Allelic variants of this sequence can be cloned by probing cDNA or genomic libraries from different individuals according to standard procedures. Allelic variants of the DNA sequence shown in SEQ ID NO:1, including those containing silent mutations and those in which mutations result in amino acid sequence changes, are within the scope of the present invention, as are proteins which are allelic variants of SEQ ID NO:2. cDNAs generated from alternatively spliced mRNAs, which retain the properties of the Zcyto10 polypeptide are included within the scope of the present invention, as are polypeptides encoded by such cDNAs and mRNAs. Allelic variants and splice variants of these sequences can be cloned by probing cDNA or genomic libraries from different individuals or tissues according to standard procedures known in the art.

The present invention further provides counterpart proteins and polynucleotides from other species ("species orthologs"). Of particular interest are Zcyto10 polypeptides from other mammalian species, including murine, porcine, ovine, bovine, canine, feline, equine, and other primates. Species orthologs of the human Zcyto10 protein can be cloned using information and compositions provided by the present invention in combination with conventional cloning techniques. For example, a cDNA can be cloned using mRNA obtained from a tissue or cell type that expresses the protein. Suitable sources of mRNA can be identified by probing Northern blots with probes designed from the sequences disclosed herein. A library is then prepared from mRNA of a positive tissue or cell line. A protein-encoding cDNA can then be isolated by a variety of methods, such as by probing with a complete or partial human or mouse cDNA or with one or more sets of degenerate probes based on the disclosed sequences. A cDNA can also be cloned using the polymerase chain reaction, or PCR (Mullis et al. U.S. Pat. No. 4,683,202), using primers designed from the sequences disclosed herein. Within an additional method, the cDNA library can be used to transform or transfect host cells, and expression of the cDNA of interest can be detected with an antibody to the protein. Similar techniques can also be applied to the isolation of genomic clones. As used and claimed, the language "an isolated polynucleotide which encodes a polypeptide, said polynucleotide being defined by SEQ ID NOs: 2, 4 12, 13, 19, 20, 25, 26, 34 and 35" includes all allelic variants and species orthologs of these polypeptides.

The present invention also provides isolated protein polypeptides that are substantially identical to the protein polypeptides of SEQ ID NO: 2 and its species orthologs. By "isolated" is meant a protein or polypeptide that is found in a condition other than its native environment, such as apart from blood and animal tissue. In a preferred form, the isolated polypeptide is substantially free of other polypeptides, particularly other polypeptides of animal origin. It is preferred to provide the polypeptides in a highly purified form, i.e. greater than 95% pure, more preferably greater than 99% pure. The term "substantially identical" is used herein to denote polypeptides having 50%, preferably 60%, more preferably at least 80%, sequence identity to the sequence shown in SEQ ID NOs: 2, 4 12, 13, 19, 20, 25, 26, 34 and 35, or their species orthologs. Such polypeptides will more preferably be at least 90% identical, and most preferably 95% or more identical to SEQ ID NO:2,or its species orthologs. Percent sequence identity is determined by conventional methods. See, for example, Altschul et al., *Bull. Math. Bio.* 48: 603–616 (1986) and Henikoff and Henikoff, *Proc. Natl. Acad. Sci. USA* 89:10915–10919 (1992). Briefly, two amino acid sequences are aligned to optimize the alignment scores using a gap opening penalty of 10, a gap extension penalty of 1, and the "blossom 62" scoring matrix of Henikoff and Henikoff (ibid.) as shown in Table 1 (amino acids are indicated by the standard one-letter codes). The percent identity is then calculated as:

$$\frac{\text{Total number of identical matches}}{\substack{\text{[length of the longer sequence plus the} \\ \text{number of gaps introduced into the longer} \\ \text{sequence in order to align the two sequences]}}} \times 100$$

TABLE 1

|   | A | R | N | D | C | Q | E | G | H | I | L | K | M | F | P | S | T | W | Y | V |
|---|---|---|---|---|---|---|---|---|---|---|---|---|---|---|---|---|---|---|---|---|
| A | 4 | | | | | | | | | | | | | | | | | | | |
| R | -1 | 5 | | | | | | | | | | | | | | | | | | |
| N | -2 | 0 | 6 | | | | | | | | | | | | | | | | | |
| D | -2 | -2 | 1 | 6 | | | | | | | | | | | | | | | | |
| C | 0 | -3 | -3 | -3 | 9 | | | | | | | | | | | | | | | |
| Q | -1 | 1 | 0 | 0 | -3 | 5 | | | | | | | | | | | | | | |
| E | -1 | 0 | 0 | 2 | -4 | 2 | 5 | | | | | | | | | | | | | |
| G | 0 | -2 | 0 | -1 | -3 | -2 | -2 | 6 | | | | | | | | | | | | |
| H | -2 | 0 | 1 | -1 | -3 | 0 | 0 | -2 | 8 | | | | | | | | | | | |
| I | -1 | -3 | -3 | -3 | -1 | -3 | -3 | -4 | -3 | 4 | | | | | | | | | | |
| L | -1 | -2 | -3 | -4 | -1 | -2 | -3 | -4 | -3 | 2 | 4 | | | | | | | | | |
| K | -1 | 2 | 0 | -1 | -3 | 1 | 1 | -2 | -1 | -3 | -2 | 5 | | | | | | | | |
| M | -1 | -1 | -2 | -3 | -1 | 0 | -2 | -3 | -2 | 1 | 2 | -1 | 5 | | | | | | | |
| F | -2 | -3 | -3 | -3 | -2 | -3 | -3 | -3 | -1 | 0 | 0 | -3 | 0 | 6 | | | | | | |
| P | -1 | -2 | -2 | -1 | -3 | -1 | -1 | -2 | -2 | -3 | -3 | -1 | -2 | -4 | 7 | | | | | |
| S | 1 | -1 | 1 | 0 | -1 | 0 | 0 | 0 | -1 | -2 | -2 | 0 | -1 | -2 | -1 | 4 | | | | |
| T | 0 | -1 | 0 | -1 | -1 | -1 | -1 | -2 | -2 | -1 | -1 | -1 | -1 | -2 | -1 | 1 | 5 | | | |
| W | -3 | -3 | -4 | -4 | -2 | -2 | -3 | -2 | -2 | -3 | -2 | -3 | -1 | 1 | -4 | -3 | -2 | 11 | | |
| Y | -2 | -2 | -2 | -3 | -2 | -1 | -2 | -3 | 2 | -1 | -1 | -2 | -1 | 3 | -3 | -2 | -2 | 2 | 7 | |
| V | 0 | -3 | -3 | -3 | -1 | -2 | -2 | -3 | -3 | 3 | 1 | -2 | 1 | -1 | -2 | -2 | 0 | -3 | -1 | 4 |

Sequence identity of polynucleotide molecules is determined by similar methods using a ratio as disclosed above.

Variant Zcyto10 polypeptides or substantially identical proteins and polypeptides are characterized as having one or more amino acid substitutions, deletions or additions. These changes are preferably of a minor nature, that is conservative amino acid substitutions (see Table 2) and other substitutions that do not significantly affect the folding or activity of the protein or polypeptide; small deletions, typically of one to about 30 amino acids; and small amino- or carboxyl-terminal extensions, such as an amino-terminal methionine residue, a small linker peptide of up to about 20–25 residues, or a small extension that facilitates purification (an affinity tag), such as a poly-histidine tract, protein A, Nilsson et al., *EMBO J.* 4:1075 (1985); Nilsson et al., *Methods Enzymol.* 198:3 (1991), glutathione S transferase, Smith and Johnson, *Gene* 67:31 (1988), or other antigenic epitope or binding domain. See, in general Ford et al., *Protein Expression and Purification* 2: 95–107 (1991). DNAs encoding affinity tags are available from commercial suppliers (e.g., Pharmacia Biotech, Piscataway, N.J.).

TABLE 2

Conservative amino acid substitutions

| | |
|---|---|
| Basic: | arginine |
| | lysine |
| | histidine |
| Acidic: | glutamic acid |
| | aspartic acid |
| Polar: | glutamine |
| | asparagine |
| Hydrophobic: | leucine |
| | isoleucine |
| | valine |
| Aromatic: | phenylalanine |
| | tryptophan |
| | tyrosine |
| Small: | glycine |
| | alanine |
| | serine |
| | threonine |
| | methionine |

The present invention further provides a variety of other polypeptide fusions [and related multimeric proteins comprising one or more polypeptide fusions]. For example, a Zcyto10 polypeptide can be prepared as a fusion to a dimerizing protein as disclosed in U.S. Pat. Nos. 5,155,027 and 5,567,584. Preferred dimerizing proteins in this regard include immunoglobulin constant region domains. Immunoglobulin-Zcyto10 polypeptide fusions can be expressed in genetically engineered cells [to produce a variety of multimeric Zcyto10 analogs]. Auxiliary domains can be fused to Zcyto10 polypeptides to target them to specific cells, tissues, or macromolecules (e.g., collagen). For example, a Zcyto10 polypeptide or protein could be targeted to a predetermined cell type by fusing a polypeptide to a ligand that specifically binds to a receptor on the surface of the target cell. In this way, polypeptides and proteins can be targeted for therapeutic or diagnostic purposes. A Zcyto10polypeptide can be fused to two or more moieties, such as an affinity tag for purification and a targeting domain. Polypeptide fusions can also comprise one or more cleavage sites, particularly between domains. See, Tuan et al., *Connective Tissue Research* 34:1–9 (1996).

The proteins of the present invention can also comprise non-naturally occurring amino acid residues. Non-naturally occurring amino acids include, without limitation, trans-3-methylproline, 2,4-methanoproline, cis-4-hydroxyproline, trans-4-hydroxyproline, N-methylglycine, allo-threonine, methylthreonine, hydroxyethylcysteine, hydroxyethylhomocysteine, nitroglutamine, homoglutamine, pipecolic acid, thiazolidine carboxylic acid, dehydroproline, 3- and 4-methylproline, 3,3-dimethylproline, tert-leucine, norvaline, 2-azaphenylalanine, 3-azaphenylalanine, 4-azaphenylalanine, and 4-fluorophenylalanine. Several methods are known in the art for incorporating non-naturally occurring amino acid residues into proteins. For example, an in vitro system can be employed wherein nonsense mutations are suppressed using chemically aminoacylated suppressor tRNAs. Methods for synthesizing amino acids and aminoacylating tRNA are known in the art. Essential amino acids in the polypeptides of the present invention can be identified according to procedures known in the art, such as site-directed mutagenesis or alanine-scanning mutagenesis [Cunningham and Wells, *Science* 244: 1081–1085 (1989)]; Bass et al., *Proc. Natl. Acad. Sci. USA* 88:4498–4502 (1991). In the latter technique, single alanine mutations are introduced at every residue in the molecule, and the resultant mutant molecules are tested for biological activity (e.g., ligand binding and signal transduction) to identify amino acid residues that are critical to the activity of the molecule. Sites of ligand-protein interaction can also be determined by analysis of crystal structure as determined by such techniques as nuclear magnetic resonance, crystallography or photoaffinity labeling. See, for example, de Vos et al., *Science* 255:306–312 (1992); Smith et al., *J. Mol. Biol.* 224:899–904 (1992); Wlodaver et al., *FEBS Lett.* 309:59–64 (1992). The identities of essential amino acids can also be inferred from analysis of homologies with related proteins.

Multiple amino acid substitutions can be made and tested using known methods of mutagenesis and screening, such as those disclosed by Reidhaar-Olson and Sauer, *Science* 241: 53–57 (1988) or Bowie and Sauer *Proc. Natl. Acad. Sci. USA* 86:2152–2156 (1989). Briefly, these authors disclose methods for simultaneously randomizing two or more positions in a polypeptide, selecting for functional polypeptide, and then sequencing the mutagenized polypeptides to determine the spectrum of allowable substitutions at each position. Other methods that can be used include phage display (e.g., Lowman et al., *Biochem.* 30:10832–10837 (1991); Ladner et al., U.S. Pat. No. 5,223,409; Huse, WIPO Publication WO 92/06204) and region-directed mutagenesis, Derbyshire et al., *Gene* 46:145 (1986); Ner et al., *DNA* 7:127 (1988).

Mutagenesis methods as disclosed above can be combined with high-throughput screening methods to detect activity of cloned, mutagenized proteins in host cells. Preferred assays in this regard include cell proliferation assays and biosensor-based ligand-binding assays, which are described below. Mutagenized DNA molecules that encode active proteins or portions thereof (e.g., ligand-binding fragments) can be recovered from the host cells and rapidly sequenced using modem equipment. These methods allow the rapid determination of the importance of individual amino acid residues in a polypeptide of interest, and can be applied to polypeptides of unknown structure.

Using the methods discussed above, one of ordinary skill in the art can prepare a variety of polypeptides that are substantially identical to SEQ ID NOs: 2, 4 12, 13, 19, 20, 25, 26, 34 and 35or allelic variants thereof and retain the properties of the wild-type protein. As expressed and claimed herein the language, "a polypeptide as defined by SEQ ID NO: 2" includes all allelic variants and species orthologs of the polypeptide.

The protein polypeptides of the present invention, including full-length proteins, protein fragments (e.g. ligand-binding fragments), and fusion polypeptides can be produced in genetically engineered host cells according to conventional techniques. Suitable host cells are those cell types that can be transformed or transfected with exogenous DNA and grown in culture, and include bacteria, fungal cells, and cultured higher eukaryotic cells. Eukaryotic cells, particularly cultured cells of multicellular organisms, are preferred. Techniques for manipulating cloned DNA molecules and introducing exogenous DNA into a variety of host cells are disclosed by Sambrook et al., *Molecular Cloning: A Laboratory Manual*, 2nd ed.(Cold Spring Harbor Laboratory Press, Cold Spring Harbor, N.Y., 1989), and Ausubel et al., ibid.

Polynucleotides, generally a cDNA sequence, of the present invention encode the above-described polypeptides. A DNA sequence which encodes a polypeptide of the present invention is comprised of a series of codons, each amino acid residue of the polypeptide being encoded by a codon and each codon being comprised of three nucleotides. The amino acid residues are encoded by their respective codons as follows.

Alanine (Ala) is encoded by GCA, GCC, GCG or GCT;
Cysteine (Cys) is encoded by TGC or TGT;
Aspartic acid (Asp) is encoded by GAC or GAT;
Glutamic acid (Glu) is encoded by GAA or GAG;
Phenylalanine (Phe) is encoded by TTC or TTT;
Glycine (Gly) is encoded by GGA, GGC, GGG or GGT;
Histidine (His) is encoded by CAC or CAT;
Isoleucine (Ile) is encoded by ATA, ATC or ATT;
Lysine (Lys) is encoded by AAA, or AAG;
Leucine (Leu) is encoded by TTA, TTG, CTA, CTC, CTG or CTT;
Methionine (Met) is encoded by ATG;
Asparagine (Asn) is encoded by AAC or AAT;
Proline (Pro) is encoded by CCA, CCC, CCG or CCT;
Glutamine (Gln) is encoded by CAA or CAG;
Arginine (Arg) is encoded by AGA, AGG, CGA, CGC, CGG or CGT;
Serine (Ser) is encoded by AGC, AGT, TCA, TCC, TCG or TCT;
Threonine (Thr) is encoded by ACA, ACC, ACG or ACT;
Valine (Val) is encoded by GTA, GTC, GTG or GTT;
Tryptophan (Trp) is encoded by TGG; and
Tyrosine (Tyr) is encoded by TAC or TAT.

It is to be recognized that according to the present invention, when a cDNA is claimed as described above, it is understood that what is claimed are both the sense strand, the anti-sense strand, and the DNA as double-stranded having both the sense and anti-sense strand annealed together by their respective hydrogen bonds. Also claimed is the messenger RNA (mRNA) which encodes the polypeptides of the present invention, and which mRNA is encoded by the above-described cDNA. A messenger RNA (mRNA) will encode a polypeptide using the same codons as those defined above, with the exception that each thymine nucleotide (T) is replaced by a uracil nucleotide (U).

In general, a DNA sequence encoding a Zcyto10 polypeptide is operably linked to other genetic elements required for its expression, generally including a transcription promoter and terminator, within an expression vector. The vector will also commonly contain one or more selectable markers and one or more origins of replication, although those skilled in the art will recognize that within certain systems selectable markers may be provided on separate vectors, and replication of the exogenous DNA may be provided by integration into the host cell genome. Selection of promoters, terminators, selectable markers, vectors and other elements is a matter of routine design within the level of ordinary skill in the art. Many such elements are described in the literature and are available through commercial suppliers.

To direct a Zcyto10 polypeptide into the secretory pathway of a host cell, a secretory signal sequence (also known as a leader sequence, prepro sequence or pre sequence) is provided in the expression vector. The secretory signal sequence may be that of the protein, or may be derived from another secreted protein (e.g., t-PA) or synthesized de novo. The secretory signal sequence is joined to the Zcyto10 DNA sequence in the correct reading frame. Secretory signal sequences are commonly positioned 5' to the DNA sequence encoding the polypeptide of interest, although certain signal sequences may be positioned elsewhere in the DNA sequence of interest (see, e.g., Welch et al., U.S. Pat. No. 5,037,743; Holland et al., U.S. Pat. No. 5,143,830).

Methods for introducing exogenous DNA into mammalian host cells include calcium phosphate-mediated transfection, Wigler et al., *Cell* 14:725 (1978); Corsaro and Pearson, *Somatic Cell Genetics* 7:603, 1981: Graham and Van der Eb, *Virology* 52:456 (1973), electroporation, Neumann et al., *EMBO J.* 1:841–845 (1982), DEAE-dextran mediated transfection, Ausubel et al., eds., *Current Protocols in Molecular Biology*, (John Wiley and Sons, Inc., NY, 1987), and liposome-mediated transfection, Hawley-Nelson et al., *Focus* 15:73 (1993); Ciccarone et al., *Focus* 15:80 (1993). The production of recombinant polypeptides in cultured mammalian cells is disclosed, for example, by Levinson et al., U.S. Pat. No. 4,713,339; Hagen et al., U.S. Pat. No. 4,784,950; Palmiter et al., U.S. Pat. No. 4,579,821; and Ringold, U.S. Pat. No. 4,656,134. Suitable cultured mammalian cells include the COS-1 (ATCC No. CRL 1650), COS-7 (ATCC No. CRL 1651), BHK (ATCC No. CRL 1632), BHK 570 (ATCC No. CRL 10314), 293 [ATCC No. CRL 1573; Graham et al., *J. Gen. Virol.* 36:59–72(1977) and Chinese hamster ovary (e.g. CHO-K1; ATCC No. CCL 61) cell lines. Additional suitable cell lines are known in the art and available from public depositories such as the American Type Culture Collection, Rockville, Md. In general, strong transcription promoters are preferred, such as promoters from SV-40 or cytomegalovirus. See, e.g., U.S. Pat. No. 4,956,288. Other suitable promoters include those from metallothionein genes (U.S. Pat. Nos. 4,579,821 and 4,601,978 and the adenovirus major late promoter.

Drug selection is generally used to select for cultured mammalian cells into which foreign DNA has been inserted. Such cells are commonly referred to as "transfectants". Cells that have been cultured in the presence of the selective agent and are able to pass the gene of interest to their progeny are referred to as "stable transfectants." A preferred selectable marker is a gene encoding resistance to the antibiotic neomycin. Selection is carried out in the presence of a neomycin-type drug, such as G-418 or the like. Selection systems may also be used to increase the expression level of the gene of interest, a process referred to as "amplification." Amplification is carried out by culturing transfectants in the presence of a low level of the selective agent and then increasing the amount of selective agent to select for cells that produce high levels of the products of the introduced genes. A preferred amplifiable selectable marker is dihydrofolate reductase, which confers resistance to methotrexate. Other drug resistance genes (e.g. hygromycin resistance, multi-drug resistance, puromycin acetyltransferase) can also be used. Alternative markers that introduce an altered phenotype, such as green fluorescent protein, or cell surface proteins such as CD4, CD8, Class I MHC, placental alkaline phosphatase may be used to sort transfected cells from untransfected cells by such means as FACS sorting or magnetic bead separation technology.

Other higher eukaryotic cells can also be used as hosts, including insect cells, plant cells and avian cells. Transformation of insect cells and production of foreign polypeptides therein is disclosed by Guarino et al., U.S. Pat. No. 5,162,222; Bang et al., U.S. Pat. No. 4,775,624; and WIPO publication WO 94/06463. The use of *Agrobacterium rhizogenes* as a vector for expressing genes in plant cells has been reviewed by Sinkar et al., *J. Biosci.* (*Bangalore*) 11:47–58 (1987). Insect cells can be infected with recombinant baculovirus, commonly derived from *Autographa californica nuclear polyhedrosis virus* (AcNPV). See, King, L. A. and Possee, R. D., *The Baculovirus Expression System: A Laboratory Guide* (Chapman & Hall, London); O'Reilly, D. R. et al., *Baculovirus Expression Vectors: A Laboratory Manual* (University Press, New York, Oxford, 1994); and, Richardson, C. D., Ed., *Baculovirus Expression Protocols. Methods in Molecular Biology*, (Humana Press, Totowa, N.J., 1995). A second method of making recombinant Zcyto10 baculovirus utilizes a transposon-based system described by Luckow, V. A, et al., *J Virol* 67:4566–79 1993). This system, which utilizes transfer vectors, is sold in the Bac-to-Bac™ kit (Life Technologies, Rockville, Md.). This system utilizes a transfer vector, pFastBac1™ (Life Technologies) containing a Tn7 transposon to move the DNA encoding the Zcyto10 polypeptide into a baculovirus genome maintained in *E. coli* as a large plasmid called a "bacmid." See, Hill-Perkins, M. S. and Possee, R. D., *J Gen Virol* 71:971–6, (1990); Bonning, B. C. et al., *J Gen Virol* 75:1551–6 (1994); and, Chazenbalk, G. D., and Rapoport, B., *J Biol Chem* 270: 1543–9 (1995). In addition, transfer vectors can include an in-frame fusion with DNA encoding an epitope tag at the C- or N-terminus of the expressed Zcyto10 polypeptide, for example, a Glu-Glu epitope tag, Grussenmeyer, T. et al., *Proc. Natl. Acad. Sci.* 82:7952–4 (1985). Using a technique known in the art, a transfer vector containing Zcyto10 is transformed into *E. Coli*, and screened for bacmids which contain an interrupted lacZ gene indicative of recombinant baculovirus. The bacmid DNA containing the recombinant baculovirus genome is isolated, using common techniques, and used to transfect *Spodoptera frugiperda* cells, e.g. Sf9 cells. Recombinant virus that expresses Zcyto10 is subsequently produced. Recombinant viral stocks are made by methods commonly used the art.

The recombinant virus is used to infect host cells, typically a cell line derived from the fall armyworm, *Spodoptera frugiperda*. See, in general, Glick and Pasternak, *Molecular Biotechnology: Principles and Applications of Recombinant DNA*, ASM Press, Washington, D.C. (1994). Another suitable cell line is the High FiveO™ cell line (Invitrogen) derived from *Trichoplusia ni* (U.S. Pat. No. 5,300,435). Commercially available serum-free media are used to grow and maintain the cells. Suitable media are Sf900 II™ (Life Technologies) or ESF 921™ (Expression Systems) for the Sf9 cells; and Ex-cellO405™ (JRH Biosciences, Lenexa, Kans.) or Express FiveO™ (Life Technologies) for the *T. ni* cells. The cells are grown up from an inoculation density of approximately 2–5×$10^5$ cells to a density of 1–2×$10^6$ cells at which time a recombinant viral stock is added at a multiplicity of infection (MOI) of 0.1 to 10, more typically near 3. Procedures used are generally described in available laboratory manuals (King, L. A. and Possee, R. D., ibid.; O'Reilly, D. R. et al., ibid.; Richardson, C. D., ibid.). Subsequent purification of the Zcyto10 polypeptide from the supernatant can be achieved using methods described herein.

Fungal cells, including yeast cells, and particularly cells of the genus *Saccharomyces*, can also be used within the present invention, such as for producing protein fragments or polypeptide fusions. Methods for transforming yeast cells with exogenous DNA and producing recombinant polypeptides therefrom are disclosed by, for example, Kawasaki, U.S. Pat. No. 4,599,311; Kawasaki et al., U.S. Pat. No. 4,931,373; Brake, U.S. Pat. No. 4,870,008; Welch et al., U.S. Pat. No. 5,037,743; and Murray et al., U.S. Pat. No. 4,845,075. Transformed cells are selected by phenotype determined by the selectable marker, commonly drug resistance or the ability to grow in the absence of a particular nutrient (e.g., leucine). A preferred vector system for use in yeast is the POT1 vector system disclosed by Kawasaki et al. (U.S. Pat. No. 4,931,373), which allows transformed cells to be selected by growth in glucose-containing media. Suitable promoters and terminators for use in yeast include those from glycolytic enzyme genes (see, e.g., Kawasaki, U.S. Pat.

No. 4,599,311; Kingsman et al., U.S. Pat. No. 4,615,974; and Bitter, U.S. Pat. No. 4,977,092 and alcohol dehydrogenase genes. See also U.S. Pat. Nos. 4,990,446; 5,063,154; 5,139,936 and 4,661,454. Transformation systems for other yeasts, including *Hansenula polymorpha, Schizosaccharomyces pombe, Kluyveromyces lactis, Kluyveromyces fragilis, Ustilago maydis, Pichia pastoris, Pichia methanolica, Pichia guillermondii* and *Candida maltosa* are known in the art. See, for example, Gleeson et al., *J. Gen. Microbiol.* 132:3459–3465 (1986) and Cregg, U.S. Pat. No. 4,882,279. *Aspergillus* cells may be utilized according to the methods of McKnight et al., U.S. Pat. No. 4,935,349. Methods for transforming *Acremonium chrysogenum* are disclosed by Sumino et al., U.S. Pat. No. 5,162,228. Methods for transforming Neurospora are disclosed by Lambowitz, U.S. Pat. No. 4,486,533.

The use of *Pichia methanolica* as host for the production of recombinant proteins is disclosed in WIPO Publications WO 97/17450, WO 97/17451, WO 98/02536, and WO 98/02565. DNA molecules for use in transforming *P. methanolica* will commonly be prepared as double-stranded, circular plasmids, which are preferably linearized prior to transformation. For polypeptide production in *P. methanolica*, it is preferred that the promoter and terminator in the plasmid be that of a *P. methanolica* gene, such as a *P. methanolica* alcohol utilization gene (AUG1 or AUG2). Other useful promoters include those of the dihydroxyacetone synthase (DHAS), formate dehydrogenase (FMD), and catalase (CAT) genes. To facilitate integration of the DNA into the host chromosome, it is preferred to have the entire expression segment of the plasmid flanked at both ends by host DNA sequences. A preferred selectable marker for use in *Pichia methanolica* is a *P. methanolica* ADE2 gene, which encodes phosphoribosyl-5-aminoimidazole carboxylase (AIRC; EC 4.1.1.21), which allows ade2 host cells to grow in the absence of adenine. For large-scale, industrial processes where it is desirable to minimize the use of methanol, it is preferred to use host cells in which both methanol utilization genes (AUG1 and AUG2) are deleted. For production of secreted proteins, host cells deficient in vacuolar protease genes (PEP4 and PRB1) are preferred. Electroporation is used to facilitate the introduction of a plasmid containing DNA encoding a polypeptide of interest into *P. methanolica* cells. It is preferred to transform *P. methanolica* cells by electroporation using an exponentially decaying, pulsed electric field having a field strength of from 2.5 to 4.5 kV/cm, preferably about 3.75 kV/cm, and a time constant (t) of from 1 to 40 milliseconds, most preferably about 20 milliseconds.

Prokaryotic host cells, including strains of the bacteria *Escherichia coli, Bacillus* and other genera are also useful host cells within the present invention. Techniques for transforming these hosts and expressing foreign DNA sequences cloned therein are well known in the art (see, e.g., Sambrook et al., ibid.). When expressing a Zcyto10 polypeptide in bacteria such as *E. coli*, the polypeptide may be retained in the cytoplasm, typically as insoluble granules, or may be directed to the periplasmic space by a bacterial secretion sequence. In the former case, the cells are lysed, and the granules are recovered and denatured using, for example, guanidine isothiocyanate or urea. The denatured polypeptide can then be refolded and dimerized by diluting the denaturant, such as by dialysis against a solution of urea and a combination of reduced and oxidized glutathione, followed by dialysis against a buffered saline solution. In the latter case, the polypeptide can be recovered from the periplasmic space in a soluble and functional form by disrupting the cells (by, for example, sonication or osmotic shock) to release the contents of the periplasmic space and recovering the protein, thereby obviating the need for denaturation and refolding.

Transformed or transfected host cells are cultured according to conventional procedures in a culture medium containing nutrients and other components required for the growth of the chosen host cells. A variety of suitable media, including defined media and complex media, are known in the art and generally include a carbon source, a nitrogen source, essential amino acids, vitamins and minerals. Media may also contain such components as growth factors or serum, as required. The growth medium will generally select for cells containing the exogenously added DNA by, for example, drug selection or deficiency in an essential nutrient which is complemented by the selectable marker carried on the expression vector or co-transfected into the host cell. *P. methanolica* cells are cultured in a medium comprising adequate sources of carbon, nitrogen and trace nutrients at a temperature of about 25° C. to 35° C. Liquid cultures are provided with sufficient aeration by conventional means, such as shaking of small flasks or sparging of fermentors. A preferred culture medium for *P. methanolica* is YEPD (2% D-glucose, 2% Bacto™ Peptone (Difco Laboratories, Detroit, Mich.), 1% Bacto™ yeast extract (Difco Laboratories), 0.004% adenine and 0.006% L-leucine).

Within one aspect of the present invention, a novel protein is produced by a cultured cell, and the cell is used to screen for a receptor or receptors for the protein, including the natural receptor, as well as agonists and antagonists of the natural ligand.

Protein Isolation:

It is preferred to purify the polypeptides of the present invention to $\geq$80% purity, more preferably to $\geq$90% purity, even more preferably $\geq$95% purity, and particularly preferred is a pharmaceutically pure state, that is greater than 99.9% pure with respect to contaminating macromolecules, particularly other proteins and nucleic acids, and free of infectious and pyrogenic agents. Preferably, a purified polypeptide is substantially free of other polypeptides, particularly other polypeptides of animal origin.

Expressed recombinant polypeptides (or chimeric polypeptides) can be purified using fractionation and/or conventional purification methods and media. Ammonium sulfate precipitation and acid or chaotrope extraction may be used for fractionation of samples. Exemplary purification steps may include hydroxyapatite, size exclusion, FPLC and reverse-phase high performance liquid chromatography. Suitable anion exchange media include derivatized dextrans, agarose, cellulose, polyacrylamide, specialty silicas, and the like. PEI, DEAE, QAE and Q derivatives are preferred, with DEAE Fast-Flow Sepharose (Pharmacia, Piscataway, N.J.) being particularly preferred. Exemplary chromatographic media include those media derivatized with phenyl, butyl, or octyl groups, such as Phenyl-Sepharose FF (Pharmacia), Toyopearl butyl 650 (Toso Haas, Montgomeryville, Pa.), Octyl-Sepharose (Pharmacia) and the like; or polyacrylic resins, such as Amberchrom CG 71 (Toso Haas) and the like. Suitable solid supports include glass beads, silica-based resins, cellulosic resins, agarose beads, cross-linked agarose beads, polystyrene beads, cross-linked polyacrylamide resins and the like that are insoluble under the conditions in which they are to be used. These supports may be modified with reactive groups that allow attachment of proteins by amino groups, carboxyl groups, sulfhydryl groups, hydroxyl groups and/or carbohydrate moieties. Examples of coupling chemistries include cyanogen bromide activation, N-hydroxysuccinimide activation, epoxide activation, sulfhydryl activation, hydrazide activation, and carboxyl and amino derivatives for carbodiimide coupling chemistries. These and other solid media are well known and widely used in the art, and are available from commercial suppliers. Methods for binding receptor polypeptides to support media are well known in the art. Selection of a particular method is a matter of routine design and is determined in part by the properties of the chosen support. See, for example, *Affinity Chromatography: Principles & Methods* (Pharmacia LKB Biotechnology, Uppsala, Sweden, 1988).

The polypeptides of the present invention can be isolated by exploitation of their properties. For example, immobilized metal ion adsorption (IMAC) chromatography can be used to purify histidine-rich proteins. Briefly, a gel is first charged with divalent metal ions to form a chelate (E. Sulkowski, *Trends in Biochem.* 3:1–7 (1985). Histidine-rich proteins will be adsorbed to this matrix with differing affinities, depending upon the metal ion used, and will be eluted by competitive elution, lowering the pH, or use of strong chelating agents. Other methods of purification include purification of glycosylated proteins by lectin affinity chromatography and ion exchange chromatography (*Methods in Enzymol.*, Vol. 182, "Guide to Protein Purification", M. Deutscher, (ed.),pp. 529–539 (Acad. Press, San Diego, 1990. Alternatively, a fusion of the polypeptide of interest and an affinity tag (e.g., polyhistidine, maltose-binding protein, an immunoglobulin domain) may be constructed to facilitate purification.

Uses

The polypeptide of the present invention has the structural characteristics of a four-helix bundle cytokine. A protein is generally characterized as a cytokine by virtue of its solubility and ability to act via cell surface receptors to signal and modulate cell proliferation. Cytokines fall into several tertiary structural fold classes, including cysteine-rich dimers (e.g., insulin, PDGF), beta-trefoil folds (e.g., FGF, IL-1), and all-alpha four helix bundles. The latter are characterized by four helices, labeled A,B,C and D, in a unique up-up-down-down topology, where two overhand loops link helices A and B and helices C and D. See, for example, Manavalan et al., *Journal of Protein Chemistry* 11(3): 321–31, (1992). The four-helix bundle cytokines are sometimes further subdivided into short chain (e.g., IL-4, I-1–2, GM-CSF) and long chain (e.g., TPO, growth hormone, leptin, IL-10), where the latter generally display longer A and D helices and overhand loops. Henceforth we shall use the term "cytokine" synonymously with "four-helix bundle cytokine". Helix A of zcyto10 includes amino acid residue 35, an isoleucine, through amino acid residue 49, an isoleucine, also defined by SEQ ID NO:14; helix B includes amino acid 91, a leucine, through amino acid 105, a threonine, also defined by SEQ ID NO:15; helix C includes amino acid residue 112, a leucine, through amino acid residue 126, a cysteine, also defined by SEQ ID NO:16; helix D includes amino acid residue 158, a valine, through amino acid residue 172, a methionine, also defined by SEQ ID NO:17.

Human Zcyto10 has an intramolecular disulfide bond between Cys33 and Cys126. The other four cysteines, Cys80, Cys132, Cys81 and Cys134 are predicted to form two intramolecular disulfide bonds in the arrangement Cys80–Cys132 and Cys81–Cys134. Residues that are predicted to be crucial for the structural stability of Zcyto10 include Cys33, Cys126, Cys80, Cys132, Cys81 and Cys134. Mutation of any one of these residues to any other residue is expected to inactivate the function of Zcyto10.

The structural stability of Zcyto10 is also dependent on the maintenance of a buried hydrophobic face on the four alpha helices. Residues Ile42, Phe46, Ile49, Leu91, Val94, Phe95, Tyr98, Leu112, Phe116, Ile119, Leu123, Val158, Leu162, Leu165, Leu168, Leu169 and Met172 are predicted to be buried in the core of the protein and if they are changed, the substituted amino acid residue must be a hydrophobic amino acid.

Residues expected to be involved in binding of Zcyto10 to a cell surface receptor include Asp57, on the overhand loop between helix A and B, and Lys160 and Glu164, charged residues predicted to be exposed on the surface of helix D. On the surface of the protein, on the loop AB and helix D areas, is a hydrophobic surface patch comprising residues Ile62, Leu71, Ile167, and Trp171. These residues may interact with a hydrophobic surface patch on a cell surface receptor.

The human Zcyto10 polypeptide of the present invention has about a 28% identity to interleukin-10 (IL-10). Mouse Zcyto10 polypeptide has approximately 24% identity to human IL-10, and about 27% identity to mouse IL-10. Human Zcyto10 polypeptide has approximately 76% identity with mouse Zcyto10 polypeptide.

Helix A of mouse Zcyto10 includes amino acid residue 35, an isoleucine, through amino acid residue 49, an arginine, of SEQ ID NO: 19, also defined by SEQ ID NO:21. Helix B of mouse Zcyto10 includes amino acid residue 91, a leucine, through amino acid residue 105, a threonine, of SEQ ID NO: 19, also defined by SEQ ID NO:22. Helix C of mouse Zcyto10 includes amino acid residue 112, a leucine, through amino acid residue 126, a cysteine, of SEQ ID NO: 19, also defined by SEQ ID NO:23. Helix D of mouse Zcyto10 includes amino acid residue 158, a valine, through amino acid residue 172, a methionine, of SEQ ID NO: 19, also defined by SEQ ID NO:24.

IL-10 is a cytokine that inhibits production of other cytokines, induces proliferation and differentiation of activated B lymphocytes, inhibits HIV-1 replication and exhibits antagonistic effects on gamma interferon. IL-10 appears to exist as a dimer formed from two alpha-helical polypeptide regions related by a 180° rotation. See, for example, Zdanov et al., *Structure:* 3(6): 591–601 (1996). IL-10 has been reported to be a product of activated Th2 T-cells, B-cells, keratinocytes and monocytes/macrophages that is capable of modulating a Th1 T-cell response. Such modulation may be accomplished by inhibiting cytokine synthesis by Th1 T-cells. See, for example, Hus et al., *Int. Immunol.* 4: 563 (1992) and D'Andrea et al., *J. Exp. Med.* 178: 1042 (1992). IL-10 has also been reported to inhibit cytokine synthesis by natural killer cells and monocytes/macrophages. See, for example, Hus et al. cited above and Fiorentino et al., *J. Immunol.* 146: 3444 (1991). In addition, IL-10 has been found to have a protective effect with respect to insulin dependent diabetes mellitus.

In analysis of the tissue distribution of the mRNA corresponding to this novel DNA, a single transcript was observed at approximately 1.2 kb. Using Clontech Multiple Tissue Northerns, the human transcript was apparent in trachea, placenta, testis, skin, salivary gland, prostate, thyroid with less expression observed in stomach and pancreas. Zcyto10 was expressed in the following mouse tissues: kidney, skeletal muscle, salivary gland, liver and skin.

The tissue specificity of Zcyto10 expression suggests that Zcyto10 may be a growth and/or maintenance factor in the trachea and salivary glands, stomach, pancreas and muscle; and may be important in local immune responses. Also, the Zcyto10 gene's location on chromosome 1q32.2 indicates that Zcyto10 is a growth/differentiation factor or important in regulating the immune response as IL-10

The present invention also provides reagents which will find use in diagnostic applications. A probe comprising the Zcyto10 DNA or RNA or a subsequence thereof can be used to determine if the Zcyto10 gene is present on chromosome 1 or if a mutation has occurred.

The present invention also provides reagents with significant therapeutic value. The Zcyto10 polypeptide (naturally occurring or recombinant), fragments thereof, antibodies and anti-idiotypic antibodies thereto, along with compounds identified as having binding affinity to the Zcyto10 polypeptide, should be useful in the treatment of conditions associated with abnormal physiology or development, including abnormal proliferation, e.g., cancerous conditions, or degenerative conditions or altered immunity.

Antibodies to the Zcyto10 polypeptide can be purified and then administered to a patient. These reagents can be combined for therapeutic use with additional active or inert ingredients, e.g., in pharmaceutically acceptable carriers or diluents along with physiologically innocuous stabilizers and excipients. These combinations can be sterile filtered and placed into dosage forms as by lyophilization in dosage vials or storage in stabilized aqueous preparations. This invention also contemplates use of antibodies, binding fragments thereof or single-chain antibodies of the antibodies including forms which are not complement binding.

The quantities of reagents necessary for effective therapy will depend upon many different factors, including means of administration, target site, physiological state of the patient, and other medications administered. Thus, treatment dosages should be titrated to optimize safety and efficacy. Typically, dosages used in vitro may provide useful guidance in the amounts useful for in vivo administration of these reagents. Animal testing of effective doses for treatment of particular disorders will provide further predictive indication of human dosage. Methods for administration include oral, intravenous, peritoneal, intramuscular, transdermal or administration into the lung or trachea in spray form by means or a nebulizer or atomizer. Pharmaceutically acceptable carriers will include water, saline, buffers to name just a few. Dosage ranges would ordinarily be expected from 1 µg to 1000 µg per kilogram of body weight per day. However, the doses by be higher or lower as can be determined by a medical doctor with ordinary skill in the art. For a complete discussion of drug formulations and dosage ranges see *Remington's Pharmaceutical Sciences*, 18$^{th}$ Ed., (Mack Publishing Co., Easton, Pa., 1996), and *Goodman and Gilman's: The Pharmacological Bases of Therapeutics*, 9$^{th}$ Ed. (Pergamon Press 1996).

Nucleic Acid-based Therapeutic Treatment

If a mammal has a mutated or lacks a Zcyto10 gene, the Zcyto10 gene can be introduced into the cells of the mammal. In one embodiment, a gene encoding a Zcyto10 polypeptide is introduced in vivo in a viral vector. Such vectors include an attenuated or defective DNA virus, such as but not limited to herpes simplex virus (HSV), papillomavirus, Epstein Barr virus (EBV), adenovirus, adeno-associated virus (AAV), and the like. Defective viruses, which entirely or almost entirely lack viral genes, are preferred. A defective virus is not infective after introduction into a cell. Use of defective viral vectors allows for administration to cells in a specific, localized area, without concern that the vector can infect other cells. Examples of particular vectors include, but are not limited to, a defective herpes virus 1 (HSV1) vector [Kaplitt et al., *Molec. Cell. Neurosci.*, 2:320–330 (1991)], an attenuated adenovirus vector, such as the vector described by Stratford-Perricaudet et al., *J. Clin. Invest.*, 90:626–630 (1992), and a defective adeno-associated virus vector [Samulski et al., *J. Virol.*, 61:3096–3101 (1987); Samulski et al. *J. Virol.*, 63:3822–3828 (1989)].

In another embodiment, the gene can be introduced in a retroviral vector, e.g., as described in Anderson et al., U.S. Pat. No. 5,399,346; Mann et al., *Cell*, 33:153 (1983); Temin et al., U.S. Pat. No. 4,650,764; Temin et al., U.S. Pat. No. 4,980,289; Markowitz et al., *J. Virol.*, 62:1120 (1988); Temin et al., U.S. Pat. No. 5,124,263; International Patent Publication No. WO 95/07358, published Mar. 16, 1995 by Dougherty et al.; and *Blood*, 82:845 (1993). Alternatively, the vector can be introduced by lipofection in vivo using liposomes. Synthetic cationic lipids can be used to prepare liposomes for in vivo transfection of a gene encoding a marker [Felgner et al., *Proc. Natl. Acad. Sci. USA*, 84:7413–7417 (1987); see Mackey et al., *Proc. Natl. Acad. Sci. USA*, 85:8027–8031 (1988)]. The use of lipofection to introduce exogenous genes into specific organs in vivo has certain practical advantages. Molecular targeting of liposomes to specific cells represents one area of benefit. It is clear that directing transfection to particular cells represents one area of benefit. It is clear that directing transfection to particular cell types would be particularly advantageous in a tissue with cellular heterogeneity, such as the pancreas, liver, kidney, and brain. Lipids may be chemically coupled to other molecules for the purpose of targeting. Targeted peptides, e.g., hormones or neurotransmitters, and proteins such as antibodies, or non-peptide molecules could be coupled to liposomes chemically. These liposomes can also be administered in spray form into the lung or trachea by means of an atomizer or nebulizer.

It is possible to remove the cells from the body and introduce the vector as a naked DNA plasmid and then re-implant the transformed cells into the body. Naked DNA vector for gene therapy can be introduced into the desired host cells by methods known in the art, e.g., transfection, electroporation, microinjection, transduction, cell fusion, DEAE dextran, calcium phosphate precipitation, use of a gene gun or use of a DNA vector transporter [see, e.g., Wu et al., *J. Biol. Chem.*, 267:963–967 (1992); Wu et al., *J. Biol. Chem.*, 263:14621–14624 (1988)].

Zcyto10 polypeptides can also be used to prepare antibodies that specifically bind to Zcyto10 polypeptides. These antibodies can then be used to manufacture anti-idiotypic antibodies. As used herein, the term "antibodies" includes polyclonal antibodies, monoclonal antibodies, antigen-binding fragments thereof such as F(ab')$_2$ and Fab fragments, and the like, including genetically engineered antibodies. Antibodies are defined to be specifically binding if they bind to a Zcyto10 polypeptide with a K$_a$ of greater than or equal to 10$^7$/M. The affinity of a monoclonal antibody can be readily determined by one of ordinary skill in the art (see, for example, Scatchard, ibid.).

Methods for preparing polyclonal and monoclonal antibodies are well known in the art (see for example, Sambrook et al., *Molecular Cloning: A Laboratory Manual, Second Edition* (Cold Spring Harbor, N.Y., 1989); and Hurrell, J. G. R., Ed., *Monoclonal Hybridoma Antibodies: Techniques and Applications* (CRC Press, Inc., Boca Raton, Fla., 1982), which are incorporated herein by reference). As would be evident to one of ordinary skill in the art, polyclonal antibodies can be generated from a variety of warm-blooded animals such as horses, cows, goats, sheep, dogs, chickens, rabbits, mice, and rats. The immunogenicity of a Zcyto10 polypeptide may be increased through the use of an adjuvant such as Freund's complete or incomplete adjuvant. A variety of assays known to those skilled in the art can be utilized to detect antibodies which specifically bind to Zcyto10 polypeptides. Exemplary assays are described in detail in *Antibodies: A Laboratory Manual*, Harlow and Lane (Eds.), (Cold Spring Harbor Laboratory Press, 1988). Representative examples of such assays include: concurrent immunoelectrophoresis, radio-immunoassays, radio-immunoprecipitations, enzyme-linked immunosorbent assays (ELISA), dot blot assays, inhibition or competition assays, and sandwich assays.

Antibodies to Zcyto10 are may be used for tagging cells that express the protein, for affinity purification, within diagnostic assays for determining circulating levels of soluble protein polypeptides, and as antagonists to block ligand binding and signal transduction in vitro and in vivo.

Within another aspect of the present invention there is provided a pharmaceutical composition comprising purified Zcyto10 polypeptide in combination with a pharmaceutically acceptable vehicle. Such compositions may be useful for modulating of cell proliferation, cell differentiation or cytokine production in the prevention or treatment of conditions characterized by improper cell proliferation, cell differentiation or cytokine production, as are further discussed herein. Moreover, Zcyto10 polypeptides of the present invention may be used in trachea-specific or tracheobronchial-specific applications, such as in the maintenance or wound repair of the tracheobronchial epithelium or cells underlying the same, in regulating mucous production or mucociliary clearance of debris or in treatment of asthma, bronchitis or other diseases of the tracheobronchial tract. It is expected that Zcyto10 polypeptide would be administered at a dose ranging between the same doses used for Zcyto10-Fc construct to doses 100-fold higher, depending upon the stability of Zcyto10 polypeptide. Therapeutic doses of Zcyto10 would range from 5 to 5000 µg/kg/day.

The Zcyto10 polypeptide of the present invention is expressed highly in salivary gland and trachea and has been found in saliva by Western blot analysis. The salivary glands synthesize and secrete a number of proteins having diverse biological functions. Such proteins facilitate lubrication of the oral cavity (e.g., mucins and proline-rich proteins), remineralization (e.g., statherin and ionic proline-rich proteins) and digestion (e.g., amylase, lipase and proteases) and provide anti-microbial (e.g., proline-rich proteins, lysozyme, histatins and lactoperoxidase) and mucosal integrity maintenance (e.g., mucins) capabilities. In addition, saliva is a rich source of growth factors synthesized by the salivary glands. For example, saliva is known to contain epidermal growth factor (EGF), nerve growth factor (NGF), transforming growth factor-alpha (TGF-$\alpha$), transforming growth factor-beta (TGF-$\beta$), insulin, insulin-like growth factors I and II (IGF-I and IGF-II) and fibroblast growth factor (FGF). See, for example, Zelles et al., *J. Dental. Res.* 74(12): 1826–32, 1995. Synthesis of growth factors by the salivary gland is believed to be androgen-dependent and to be necessary for the health of the oral cavity and gastrointestinal tract.

Thus, Zcyto10 polypeptides, agonists or antagonists thereof may be therapeutically useful in the regeneration of the gastrointestinal tract or oral cavity. To verify this presence of this capability in Zcyto10 polypeptides, agonists or antagonists of the present invention, such Zcyto10 polypeptides, agonists or antagonists are evaluated with respect to their ability to break down starch according to procedures known in the art. Zcyto10 polypeptides, agonists or antagonists thereof may be useful in the treatment of asthma and other diseases of the tracheobronchial tract, such as bronchitis and the like, by intervention in the cross-regulation of Th1 and Th2 lymphocytes, regulation of growth, differentiation and cytokine production of other inflammatory cellular mediators, such as eosinophils, mast cells, basophils, neutrophils and macrophages. Zcyto10 polypeptides, agonists or antagonists thereof may also modulate muscle tone in the tracheobronchial tract.

Zcyto10 polypeptides can also be used to treat a number of skin conditions either systemically or locally when placed in an ointment or cream, for example eczema, psoriasis or dry skin conditions in general or as related skin attentions. Also the Zcyto10 polypeptide can be directly injected into muscle to treat muscle atrophy in the elderly, the sick or the bed-ridden.

Radiation hybrid mapping is a somatic cell genetic technique developed for constructing high-resolution, contiguous maps of mammalian chromosomes [Cox et al., *Science* 250:245–250 (1990)]. Partial or full knowledge of a gene's sequence allows the designing of PCR primers suitable for use with chromosomal radiation hybrid mapping panels. Commercially available radiation hybrid mapping panels which cover the entire human genome, such as the Stanford G3 RH Panel and the GeneBridge 4 RH Panel (Research Genetics, Inc., Huntsville, Ala.), are available. These panels enable rapid, PCR based, chromosomal localizations and ordering of genes, sequence-tagged sites (STSs), and other nonpolymorphic- and polymorphic markers within a region of interest. This includes establishing directly proportional physical distances between newly discovered genes of interest and previously mapped markers. The precise knowledge of a gene's position can be useful in a number of ways including: 1) determining if a sequence is part of an existing contig and obtaining additional surrounding genetic sequences in various forms such as YAC-, BAC- or cDNA clones, 2) providing a possible candidate gene for an inheritable disease which shows linkage to the same chromosomal region, and 3) for cross-referencing model organisms such as mouse which may be beneficial in helping to determine what function a particular gene might have.

The results showed that the Zcyto10 gene maps 889.26 cR_3000 from the top of the human chromosome 1 linkage group on the WICGR radiation hybrid map. Proximal and distal framework markers were D1S504 and WI-9641 (D1S2427), respectively. The use of the surrounding markers positions the Zcyto10 gene in the 1q32.2 region on the integrated LDB chromosome 1 map (The Genetic Location Database, University of Southhampton, WWW server: http://cedar.genetics.soton.ac.uk/public_html/). Numerous genes have been mapped to the 1q32.2 region of chromosome 1. In particular, mutations in this region have been found to result in van der Woude syndrome, associated with malformation of the lower lip that is sometimes associated with cleft palate. Thus, the Zcyto10 gene, which is expressed in the salivary gland, may be used in gene therapy of this syndrome. If a mammal has a mutated or lacks a Zcyto10 gene, the Zcyto10 gene can be introduced into the cells of the mammal.

Another aspect of the present invention involves antisense polynucleotide compositions that are complementary to a segment of the polynucleotide set forth in SEQ ID NOs: 1,3 18 and 33. Such synthetic antisense oligonucleotides are designed to bind to mRNA encoding Zcyto10 polypeptides and inhibit translation of such mRNA. Such antisense oligonucleotides are useful to inhibit expression of Zcyto10 polypeptide-encoding genes in cell culture or in a subject.

The present invention also provides reagents which will find use in diagnostic applications. For example, the Zcyto10 gene, a probe comprising Zcyto10 DNA or RNA or a subsequence thereof can be used to determine if the Zcyto10 gene is present on chromosome 1 or if a mutation has occurred. Detectable chromosomal aberrations at the Zcyto10 gene locus include but are not limited to aneuploidy, gene copy number changes, insertions, deletions, restriction site changes and rearrangements. Such aberrations can be detected using polynucleotides of the present invention by employing molecular genetic techniques, such as restriction fragment length polymorphism (RFLP) analysis, short tandem repeat (STR) analysis employing PCR techniques, and other genetic linkage analysis techniques known in the art [Sambrook et al., ibid., Ausubel, et. al., ibid.; Marian, A. J., *Chest*, 108: 255–265, (1995)].

Those skilled in the art will recognize that the sequences disclosed in SEQ ID NOs: 2, 4 12, 13, 19, 20, 25, 26, 34 and 35 represent a single alleles of the human and mouse Zcyto10 genes and polypeptides, and that allelic variation and alternative splicing are expected to occur. Allelic variants can be cloned by probing cDNA or genomic libraries from different individuals according to standard procedures. Allelic variants of the DNA sequence shown in SEQ ID NOs: 1, 3, 18 and 33 including those containing silent mutations and those in which mutations result in amino acid sequence changes, are within the scope of the present invention.

The sequence of Zcyto10 has 7 message instability motifs in the 3' untranslated region at positions 706, 813, 855 and 906 of SEQ ID NO:1. Treatment of cells expressing Zcyto10 with cycloheximide can alleviate this message instability. See Shaw, G. et. al., *Cell* 46: 659–667 (1986). Furthermore, the AT rich 3' untranslated region can be genetically altered or removed to further promote message stability.

Use of Zcyto10 to Promote Wound Healing

The data of Example 4 shows that Zcyto10 plays a role in wound healing. Thus, Zcyto10 can be applied to a wound or a burn to promote wound healing. Zctyo10 may be administered systemically in a dosage of from 1 to 100 μg per kilogram weight of the individual. Zcyto10 may also be applied to a wound by means of a salve or ointment which contains from 1 ng to 1 mg of Zcyto10 to gram of salve or ointment. See *Remington's Pharmaceutical Sciences*, 18$^{th}$ Ed., (Mack Publishing Co., Easton, Pa., 1996). Zcyto10 should be placed on a cleaned wound on a daily basis until the wound has healed.

Use of Zcyto10 to Increase Platelet Count

As can be seen below in Example 7, we have discovered that Zcyto10 can be used to increase platelet count. This is especially important to cancer patients who experience thrombocytopenia due to chemotherapy or radiation therapy. The Zcyto10 can be administered therapeutically in with a pharmaceutically acceptable carrier.

The invention is further illustrated by the following non-limiting examples.

EXAMPLE 1

Cloning of Zcyto10

The full length sequence of zcyto10×1 (the longer form) and zcyto10×2 (the shorter form) was elucidated by using 3' RACE® and submitting two fragments generated to sequencing (SEQ ID NO:10 and SEQ ID NO:11), then artificially splicing together by computer the est sequence shown in SEQ ID NO:5 with the overlapping sequence from the two 3' race fragments.

An oligo, zc15907 (SEQ ID NO: 6), was designed to the area just upstream (5') of the putative methionine for zcyto10. Further downstream, another oligo, zc15906 (SEQ ID NO: 7), was designed to the area just upstream of the signal sequence cleavage site. These oligos were used in 3' RACE reactions on human trachea marathon cDNA. ZC15907 was used in the primary 3' race reaction and zc15906 was used in the nested 3' race reaction. The MARATHON cDNA was made using the Marathon cDNA Amplification Kit (Clontech, Palo Alto, Calif.) according to the manufacturer's instructions, starting with human trachea mRNA purchased from Clontech.

The PCR reactions were run according to the manufacturer's instructions in the Marathon cDNA Amplification Kit with some modification in the thermal cycling parameters. The cycling parameters used in the primary PCR reaction were:
94° C. 1 min 30 sec 1×
94° C. 15 sec 68° C. 1 min 30×
72° C. 7 min 1×

The cycling parameters used in the nested PCR reaction were: 94° C. 1 min 30 sec 1×, 94° C. 15 sec 68° C. 1 min 20 sec, 30×72° C. 7 min 1×.

The resulting products were run out on a 1.2% agarose gel (Gibco agarose) and two main bands were seen, approximately 80 bp apart. The bands were cut out and gel purified using QIAEX™ resin (Qiagen) according to the manufacturer's instructions. These fragments were then subjected to sequencing, allowing the full length sequence of zcyto10 to be discerned.

EXAMPLE 2

Northern Blot Analysis

Human multiple tissue blots I, II, III, and a RNA Master Dot Blot (Clontech) were probed to determine the tissue distribution of zcyto10. A 45-mer antisense oligo, SEQ ID NO:9, was designed using the est sequence (SEQ ID NO: 5) bp 100–145) and used for the probe.

15 pm of SEQ ID NO: 9 were end labeled with $^{32}$P using T4 polynucleotide kinase (Gibco-BRL). The labeling reaction contained 2 μl 5× forward kinase reaction buffer (Gibco-BRL), 1 ul T4 kinase, 15 pm SEQ ID NO:9, 1 ul 6000 Ci/mmol $^{32}$P gamma-ATP (Amersham) and water to 10 ul. The reaction was incubated 30 minutes at 37° C. Unincorporated radioactivity was removed with a NucTrap Probe Purification Column (Stratagene). Multiple tissue northerns and a human RNA Master Blot (Clontech) were prehybridized at 50° C. three hours in 10 ml ExpressHyb (Clontech) which contained 1 mg of salmon sperm DNA and 0.3 mg human cot1 DNA (Gibco-BRL), both of which were boiled 3 minutes, iced 2 minutes and then added to the ExpressHyb. Hybridization was carried out over night at 50 C Initial wash conditions were as follows: 2×SSC, 0.1% SDS RT for 40 minutes with several wash solution changes, then 1×SSC, 0.1% SDS at 64° C. (Tm-10) for 30 minutes. Filters were then exposed to film two days.

Expression of zcyto10 on the northern blots revealed about a 1.2 kb band in trachea, a faint 1.5 kb band in stomach and fainter bands of both sizes in pancreas. The dot blots showed the presence of zcyto10 in trachea, salivary gland, placenta, testis, skin, prostate gland, adrenal gland and thyroid.

In the mouse it was found in the kidney, skeletal muscle, salivary gland, liver and skin.

EXAMPLE 3

Chromosomal Assignment and Placement of Zcyto10

Zcyto10 was mapped to chromosome 1 using the commercially available version of the "Stanford G3 Radiation Hybrid Mapping Panel" (Research Genetics, Inc., Huntsville, Ala.); The "Stanford G3 RH Panel" contains PCRable DNAs from each of 83 radiation hybrid clones of the whole human genome, plus two control DNAs (the RM donor and the A3 recipient). A publicly available WWW server (http://shgc-www.stanford.edu) allows chromosomal localization of markers.

For the mapping of Zcyto10 with the "Stanford G3 RH Panel", 20 μl reactions were set up in a PCRable 96-well microtiter plate (Stratagene, La Jolla, Calif.) and used in a "RoboCycler Gradient 96" thermal cycler (Stratagene). Each of the 85 PCR reactions consisted of 2 μl 10× KlenTaq PCR reaction buffer (CLONTECH Laboratories, Inc., Palo Alto, Calif.), 1.6 μl dNTPs mix (2.5 mM each, PERKIN-ELMER, Foster City, Calif.), 1 μl sense primer, SEQ ID NO: 6, 5' ATT CCT AGC TCC TGT GGT CTC CAG 3', 1 μl antisense primer, (SEQ ID NO: 8) 5' TCC CAA ATT GAG TGT CTT CAG T 3', 2 μl "RediLoad" (Research Genetics, Inc., Huntsville, Ala.), 0.4 μl 50× Advantage KlenTaq Polymerase Mix (Clontech Laboratories, Inc.), 25 ng of DNA from an individual hybrid clone or control and x μl ddH$_2$O for a total volume of 20 μl. The reactions were overlaid with an equal amount of mineral oil and sealed. The PCR cycler conditions were as follows: an initial 1 cycle 5 minute denaturation at 95° C., 35 cycles of a 1 minute denaturation at 95° C., 1 minute annealing at 66° C. and 1.5 minute extension at 72° C., followed by a final 1 cycle extension of 7 minutes at 72° C. The reactions were separated by electrophoresis on a 2% agarose gel (Life Technologies, Gaithersburg, Md.).

The results showed linkage of Zcyto10 to the framework maker SHGC-36215 with a LOD score of >10 and at a distance of 14.67cR_10000 from the marker. The use of surrounding markers positions Zcyto10 in the 1q32.2 region on the integrated LDB chromosome 1 map (The Genetic Location Database, University of Southhampton, WWW server: http://cedar.genetics.soton.ac.uk/public_html/).

EXAMPLE 4

Use of Zcyot10 to Promote Wound Healing

Normal adult female Balb/C mice were used in the present study. They were housed in animal care facilities with a 12-hour light-dark cycle, given water and laboratory rodent chow ad libitum during the study. They were individually caged from the day of surgery.

On the day of surgery, the animals were anesthetized with ketamine (Vetalar, Aveco Inc., Ft. Dodge, Iowa) 104 mg/kg plus Xylazine (Rompun, Mobey Corp., Shawnee, Kans.) 7 mg/kg in sterile (0.2 μ-filtered) phosphate buffered saline (PBS) by intraperitoneal injection. The hair on their backs was clipped and the skin depilated with NAIR® (Carter-Wallace, New York, N.Y.), then rinsed with water. 100% aloe vera gel was applied to counteract the alkaline burn from the NAIR® treatment, then the animals were placed on circulating water heating pads until the skin and surrounding fur were dry.

The animals were then anesthetized with metofane (Pittman Moore, Mundelein, N.J.) and the depilated dorsum wiped with 70% ethanol. Four excisions, each of 0.5-cm square were made through the skin and panniculus carnosus over the paravertebral area at the level of the thoracic-lumbar vertebrae. The wounds and surrounding depilated skin were covered with an adhesive, semipermeable occlusive dressing, BIOCLUSIVE® (Johnson & Johnson, Arlington, Tex.). The cut edge of the excision was traced through the BIOCLUSIVE® onto an acetate transparency for later assessment of closure parameters.

Control skin and wounded skin at different time points (7 hours, 15 hours and 24 hours) were processed using the Qiagen RNeasy Midi kit. Briefly, skin (control and wounded areas) were weighed and homogenized in appropriate volume of lysis buffer (RLT). The lysates were spun to remove tissue debris and equal volume of 70% ethanol was added to the lysates; mixed well and loaded on column. The samples were spun five minutes and washed once with 3.8 ml of RW1 buffer, then twice with RPE (2.5 ml each). The total RNA's were eluted with RNase-free water. The expression level of the skin samples were measured using real time PCR (Perkin Elmer ABI Prism 7700 Sequence Detector).

The experiment was designed with a non template control, a set of standard and the skin samples. Mouse kidney total RNA was use for the standard curve. Three sets of skin total RNA's (25 ng) were used in this experiment 7 hours (control and wounded); 15 hours (control and wounded), 24 hours (control and wounded). Each sample was done in triplicate by One-Step RT-PCR on the 7700 sequence detector. The in-house forward primer SEQ ID NO:36, reverse primer SEQ ID NO:37, and the Perkin Elmer's TaqMan probe (ZG-7-FAM) were used in the experiment. The condition of the One Step RT-PCR was as follow: (RT step) 48° C. for 30 minutes, (40 cycles PCR step) 95° C. for 10 minutes, 95° C. for 15 second, 60° C. for 1 minute.

The expression level of cyto10 in the control skin samples at 7 hours and 15 hours were comparable at 2.46 ng/ml and 2.61 ng/ml respectively. From the control skin sample at 24 hours, the expression level of Zcyto10 was zero. The expression level of cyto10 from wounded skin at 7 hours was at 5.17 ng/ml (more than two fold increase compared to that of the control sample). The expression level of cyto10 from wounded skin at 15 hours was at 14.45 ng/ml (5.5 fold increase compared to that of the control sample). The expression level of cyto10 from wounded skin at 24 hours was at 5.89 ng/ml. A repeat experiment also included a negative control (yeast tRNA) gave the similar trend and the result of yeast tRNA was near zero. The result suggested that the amplification was real and mouse specific.

These data suggest that Zcyto10 plays a role in the repair of wounded because the expression level of Zcyto10 from wounded tissue was up compared to that of the control sample and it increased and decreased after time. Thus, Zcyto10 can be applied to wounds to promote wound healing.

EXAMPLE 5

Transgenic Mice

Transgenic mice were produced which expressed Zcyto10 either under the albumin or the metallothionine promoter. At birth, several of the mice had a shiny appearance and had limited movement. The skin of these mice was tight and wrinkled, several also had a whisker-like hair on the lower lip. The nostril and mouth areas, the extremities and the tail were swollen.

One transgenic mouse, in which the albumin promoter was used survived until day three and was severely growth retarded. There was no ear development and the development of the toes was diminished. All animals were sacrificed when they were moribund on days 1, 2 or 3. Tails and liver samples were collected and they were fixed in situ in 10% neutral formalin embedded in paraffin, and sectioned at 3 micrometers and stained with H&E. All mice with this phenotype were transgenic and had low to high expression of Zcyto10.

No significant changes were observed in the majority of the tissues except for the skin. The skin of the zcyto10 expressing pups, particularly the those mice which had a high expression level of Zcyto10, tended to be thicker than the non-expressing pups. The stratum granulosum in these pups appeared to be reduced in thickness as compared to the non-expressing pups, while the stratum spinosum was thicker due to increased cell layers and/or increased cell diameter.

In addition to the changes in the epidermis, the dermis of one mouse having medium expression of Zcyto10 was focally moderately expanded by mucinous material.

EXAMPLE 6

Purification of Zcyto10 from a Cell Culture Medium

Zcyto10 produced by CHO cells was isolated from the cell culture medium using a two step method involving a cation exchange chromatography and size exclusion chromatography.

A. Cation Exchange Chromatography Step.

Materials Used 2.2 cm diameter (D)×6 cm height (H) column (AMICON) packed with a SP-650M cation exchange resin, which is a TOYOPEARL ion exchange resin having covalently bonded sulfopropyl (SP) groups.

Fifteen (15)liters of culture medium from baby hamster kidney (BHK) cells which had been transfected with a Zcyto10 containing plasmid was collected. The pH of the culture medium was adjusted to pH5 with 2N HCl. The above-described packed column was equilibrated with 50 mM sodium acetate, NaAc, pH5.0. The culture medium was loaded onto the column at the rate of 20 column-volumes (cv)/hr at approximately 8 ml/min. When the loading was done the column was washed with 10 cv of 50 mM NaAc, pH5.0. The material in the column was then eluted with 20 cv of NaCl gradient in 50 mM NaAc, pH 5.0. The NaCl gradient ranged from 0 to 0.5 M NaCl. This concentrated the material in the culture medium from 15 liters to 170 ml.

The resultant 170 ml harvest was further concentrated to about 5 ml with a spin 5 thousand cut-off centrifugal concentrator (Millipore, Inc. Bedford, Mass.).

B. Size Exclusion (S-100) Gel Filtration Step

Materials Used.

Column 1.6 cm (diameter)×93 cm (height)

S-100 gel (Pharmacia, Piscataway, N.J.)

The 5 ml harvest was then loaded onto the above-described column containing S-100 gel. The column had been equilibrated with 5× phosphate buffered saline to bring the pH of the column to about 7.0. Zcyto10 was isolated from the contaminants by using 1×PBS at a flow rate of 1.5 ml/min. Fractions were collected at 2 ml increments. The Zcyto10 polypeptide came out in fractions 52–64 at about 90 minutes after the elution had been initiated as determined by sodium dodecyl sulfate (SDS) polyacrylamide gel electrophoresis which were stained with Coomassie Blue. The gel revealed one band at the predicted molecular weight of about 14 kDa.

EXAMPLE 7

Cloning of Murine Zcyto10

PCR primers 5' MARATHON RACE™ (Clontech, Palo Alto, Calif.) primer set SEQ ID NO: 38 attached to MARATHON™ API adapter, nested with SEQ ID NO:39 attached to AP2 MARATHON™ adapter, with 3' MARATHON RACE™ primer set SEQ ID NO: 40 attached to MARATHON RACE™ API adapter, nested with SEQ ID NO:41 attached to MARATHON RACE™ AP2 adapter and 5' and 3' race was performed on mouse skin MARATHON RACE™ cDNA. Several fragments were from these reactions were gel purified and sequenced, allowing the elucidation of the full length coding sequence of the mouse zcyto10, plus some 5' and 3' UTR sequence. Two murine Zcyto10 variants were discovered, namely SEQ ID NOs: 18 and 19 and SEQ ID NOs: 33 and 34. The clones were amplified by PCR using primers SEQ ID NOs:42 and 43.

EXAMPLE 8

Adenovirus Administration of Zcyto10 to Normal Mice

Zcyto10 was administered by adenovirus containing the Zcyto10 gene. There were three groups of mice as described below. The adenovirus was injected intravenously into C57B1/6 male and female mice. All mice received bromodeoxyuridine (BrdU) in their drinking water 3 days before sacrifice. This allowed for detection of cell proliferation by histologic methods. Parameters measured included weight change, complete blood counts, serum chemistries, histology, organ weights and cell proliferation by BrdU.

| Experimental Design | |
|---|---|
| Group 1 | Zcyto10X1 (SEQ ID NO: 18)/pAC-CMV/AdV $1 \times 10^{11}$ particles/dose (9 females, 9 males sacrificed on day 21) (2 females, 2 males sacrificed on day 11) total number = 22 mice. |
| Group 2 | null CMV/AdV control $1 \times 10^{11}$ particles/dose (10 females, 10 males sacrificed on day 21) (2 females, 2 males sacrificed on day 11) total number = 24 mice. |
| Group 3 | no treatment (5 females, 5 males) total number = 10. |

Results

The most striking effect was a significant increase in platelet count which was observed in male and female mice treated with Zcyto10-adenovirus compared to empty adenovirus control. This was accompanied in male mice by a decrease hematocrit and increased spleen and liver weight. The thymus weight was decreased in males also. In contrast Zcyto10-adenovirus treated female mice showed signifi cantly increased white blood cell counts which were consisted primarily of increased lymphocyte and neutrophil counts compared to the empty virus control.

These results suggest that hematopoiesis is effected by Zcyto10 treatment, but except for the increased platelet count which effected both sexes, other effects are sex specific.

Other effects included the following.

Female glucose levels were lower in treated groups while those of the males showed no significant change.

Blood Urea Nitrogen (BUN) was higher in both male and female treated groups.

Female alkaline phosphatase was higher in the treated group while the males showed no significant change.

What is claimed is:

1. An isolated antibody which binds to a polypeptide consisting of SEQ ID NO:2.

2. The isolated antibody according to claim 1 wherein said polypeptide consists of amino acid residues 25 to 176 of SEQ ID NO:2.

3. The isolated antibody according to claim 1, wherein said isolated antibody further comprises a label.

4. The isolated antibody according to claim 1, wherein said isolated antibody is a polyclonal antibody.

5. The isolated antibody according to claim 1, wherein said isolated antibody is a monoclonal antibody.

6. A hybridoma which produces a monoclonal antibody according to claim 5.

7. An isolated antibody which binds to a Zcyto10 polypeptide consisting of amino acid residues 35 to 49 of SEQ ID NO:2.

8. An isolated antibody which binds to a Zcyto10 polypeptide consisting of amino acid residues 57 to 71 of SEQ ID NO:2.

9. An isolated antibody which binds to a Zcyto10 polypeptide consisting of amino acid residues 91 to 105 of SEQ ID NO:2.

10. An isolated antibody which binds to a Zcyto10 polypeptide consisting of amino acid residues 112 to 126 of SEQ ID NO:2.

11. An isolated antibody which binds to a Zcyto10 polypeptide consisting of amino acid residues 158 to 172 of SEQ ID NO:2.

12. An anti-idiotypic antibody which binds to an antibody according to any one of claims 1,2,7,9,10,11.

13. An isolated antibody fragment which binds to a polypeptide consisting of SEQ ID NO:2.

14. The antibody fragment according to claim 13, wherein said polypeptide consists of amino acid residues 25 to 176 of SEQ ID NO:2.

15. The antibody fragment according to claim 13, wherein said isolated antibody fragment further comprises a label.

16. The antibody fragment according to claim 13, wherein the antibody fragment is an F(ab')$_2$ fragment.

17. The antibody fragment of claim 13, wherein the antibody fragment is an Fab fragment.

18. The antibody fragment of claim 13, wherein the antibody fragment is a variable region of a monoclonal antibody.

19. An isolated antibody fragment which binds to a Zcyto10 polypeptide, wherein said polypeptide consists of the amino acid sequence selected from the group consisting of:
  (i) amino acid residues 35 to 49 of SEQ ID NO:2;
  (ii) amino acid residues 57 to 71 of SEQ ID NO:2;
  (iii) amino acid residues 57 to 71 of SEQ ID NO:2;
  (iv) amino acid residues 91 to 105 of SEQ ID NO:2;
  (v) amino acid residues 91 to 105 of SEQ ID NO:2;
  (vi) amino acid residues 112 to 126 of SEQ H) NO:2;
  (vii) amino acid residues 112 to 126 of SEQ ID NO:2;
  (viii) amino acid residues 158 to 172 of SEQ H) NO:2; and
  (ix.) amino acid residues 158 to 172 of SEQ ID NO:2.

20. A method of producing an antibody to a Zcyto10 polypeptide consisting of:
inoculating an animal with a Zcyto10 polypeptide consisting of an amino acid sequence of SEQ ID NO:2, wherein the Zcyto10 polypeptide elicits an immune response in the animal to produce the antibody; and isolating the antibody from the animal.

21. The antibody produced by the method of claim 20, wherein the antibody binds to a Zcyto10 polypeptide consisting of SEQ ID NO:2.

22. The anti body produced by the method of claim 20, wherein the antibody is a polyclonal antibody.

* * * * *

UNITED STATES PATENT AND TRADEMARK OFFICE
CERTIFICATE OF CORRECTION

| | |
|---|---|
| PATENT NO. | : 7,151,166 B2 |
| APPLICATION NO. | : 10/789968 |
| DATED | : December 19, 2006 |
| INVENTOR(S) | : Darrell C. Conklin and Betty A. Haldeman |

It is certified that error appears in the above-identified patent and that said Letters Patent is hereby corrected as shown below:

Column 11, line 35, "modem" should read --modern--.

Column 17, line 45, "I-1-2" should read --IL-2--.

In claim 19, at (vi), "H" should read --ID--.

In claim 19, at (viii), "H" should read --ID--.

Signed and Sealed this

Twentieth Day of March, 2007

JON W. DUDAS
*Director of the United States Patent and Trademark Office*